(12) United States Patent
Valaie

(10) Patent No.: US 8,308,731 B2
(45) Date of Patent: Nov. 13, 2012

(54) VERTEBROPLASTY ALL IN ONE MIXER

(75) Inventor: Arman H. Valaie, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 1092 days.

(21) Appl. No.: 12/202,748

(22) Filed: Sep. 2, 2008

(65) Prior Publication Data

US 2010/0054075 A1    Mar. 4, 2010

(51) Int. Cl.
*A61B 17/58*    (2006.01)

(52) U.S. Cl. ............... 606/92; 606/93; 366/6; 366/27; 366/139

(58) Field of Classification Search .............. 366/6, 27, 366/139; 606/92, 93
See application file for complete search history.

(56) References Cited

U.S. PATENT DOCUMENTS

| | | |
|---|---|---|
| 2,224,967 A | 12/1940 | Kaye |
| 2,764,157 A | 9/1956 | Oliva et al. |
| 2,825,134 A | 3/1958 | Hicks |
| 3,831,903 A | 8/1974 | Harmel, Jr. |
| 4,277,184 A | 7/1981 | Solomon |
| 5,348,391 A | 9/1994 | Murray |
| 5,842,785 A | 12/1998 | Brown |
| 6,395,006 B1 | 5/2002 | Burchett |
| 7,306,361 B2 | 12/2007 | Coffeen et al. |
| 7,311,436 B2 | 12/2007 | Barker et al. |
| 7,842,040 B2 * | 11/2010 | Rabiner et al. ............ 606/92 |
| 2004/0267272 A1 * | 12/2004 | Henniges et al. ............ 606/93 |
| 2008/0033447 A1 | 2/2008 | Sand |

FOREIGN PATENT DOCUMENTS

| | | |
|---|---|---|
| EP | 0528447 | 2/1993 |
| EP | 1020167 | 7/2000 |

* cited by examiner

*Primary Examiner* — Yogendra Gupta
*Assistant Examiner* — Robert J Grun
(74) *Attorney, Agent, or Firm* — Woodard, Emhardt, Moriarty, McNett & Henry LLP

(57) ABSTRACT

In at least one embodiment of the present invention, a device for mixing and dispensing a bone cement mixture is provided. The device comprises an injector housing having a chamber for containing a first and a second bone cement component and a second housing having a chamber for containing a flexible wire mixing element. A plunger actuates within the chamber of the second housing to transfer the wire mixing element to the injector housing for mixing the first and second bone cement components to form the bone cement mixture. The plunger rotates the wire mixing element to mix the bone cement mixture. Thereafter, the wire mixing element is withdrawn from the injector housing and the injector housing is assembled with an injector handle. A plunger coupled to the injector handle advances through the injector chamber to dispense the bone cement mixture from the device.

27 Claims, 12 Drawing Sheets

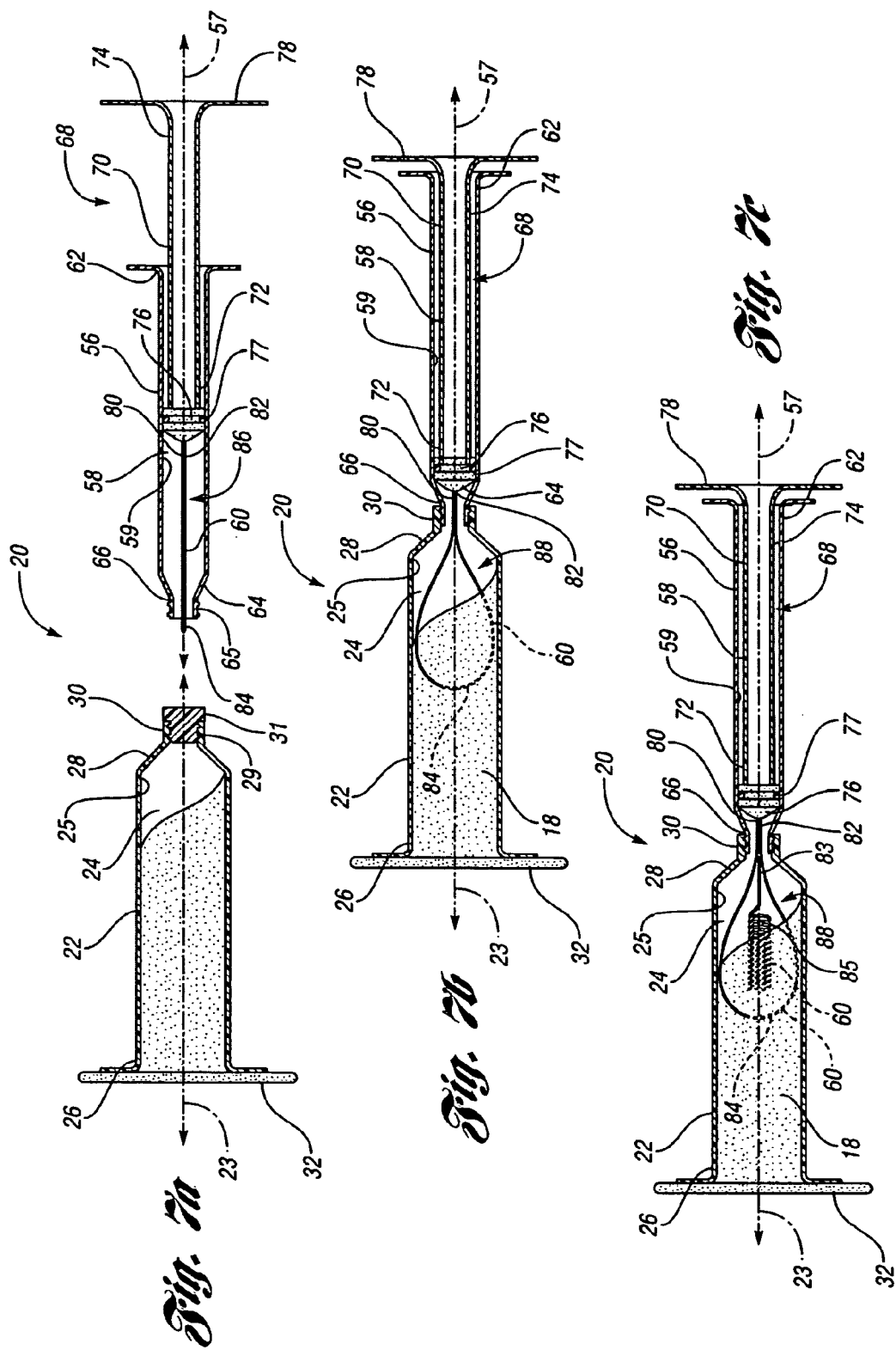

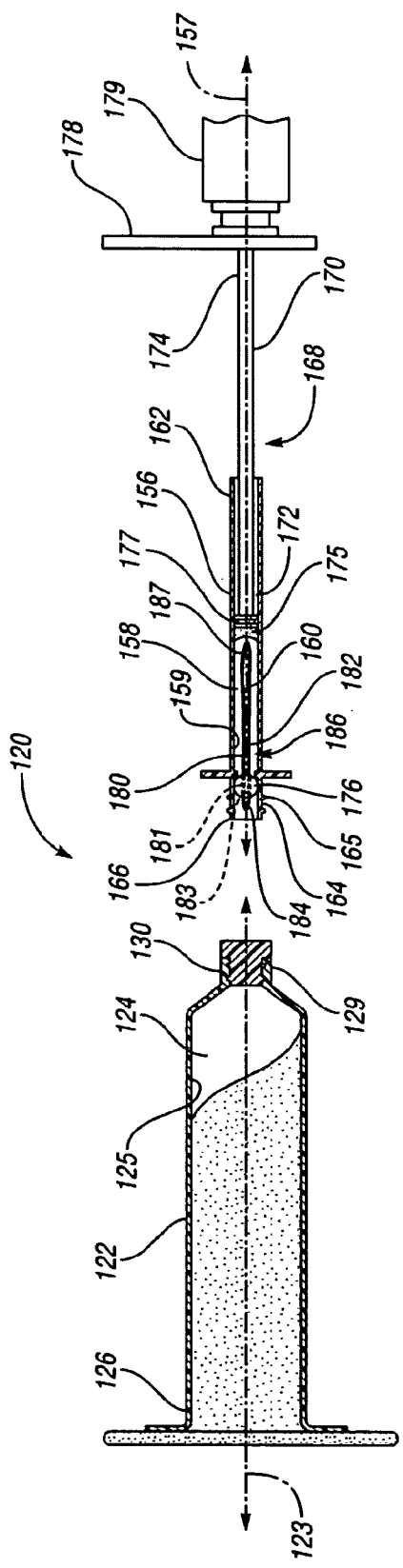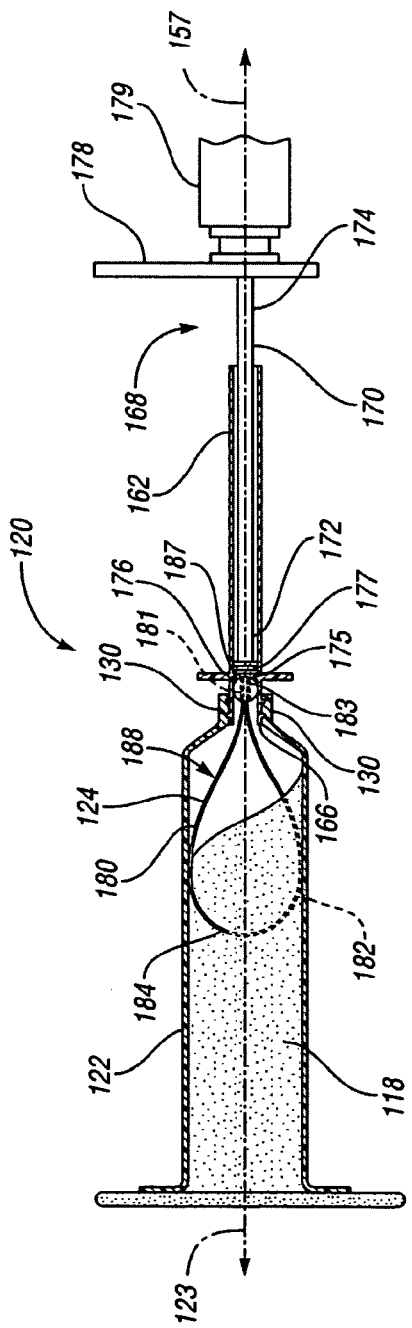

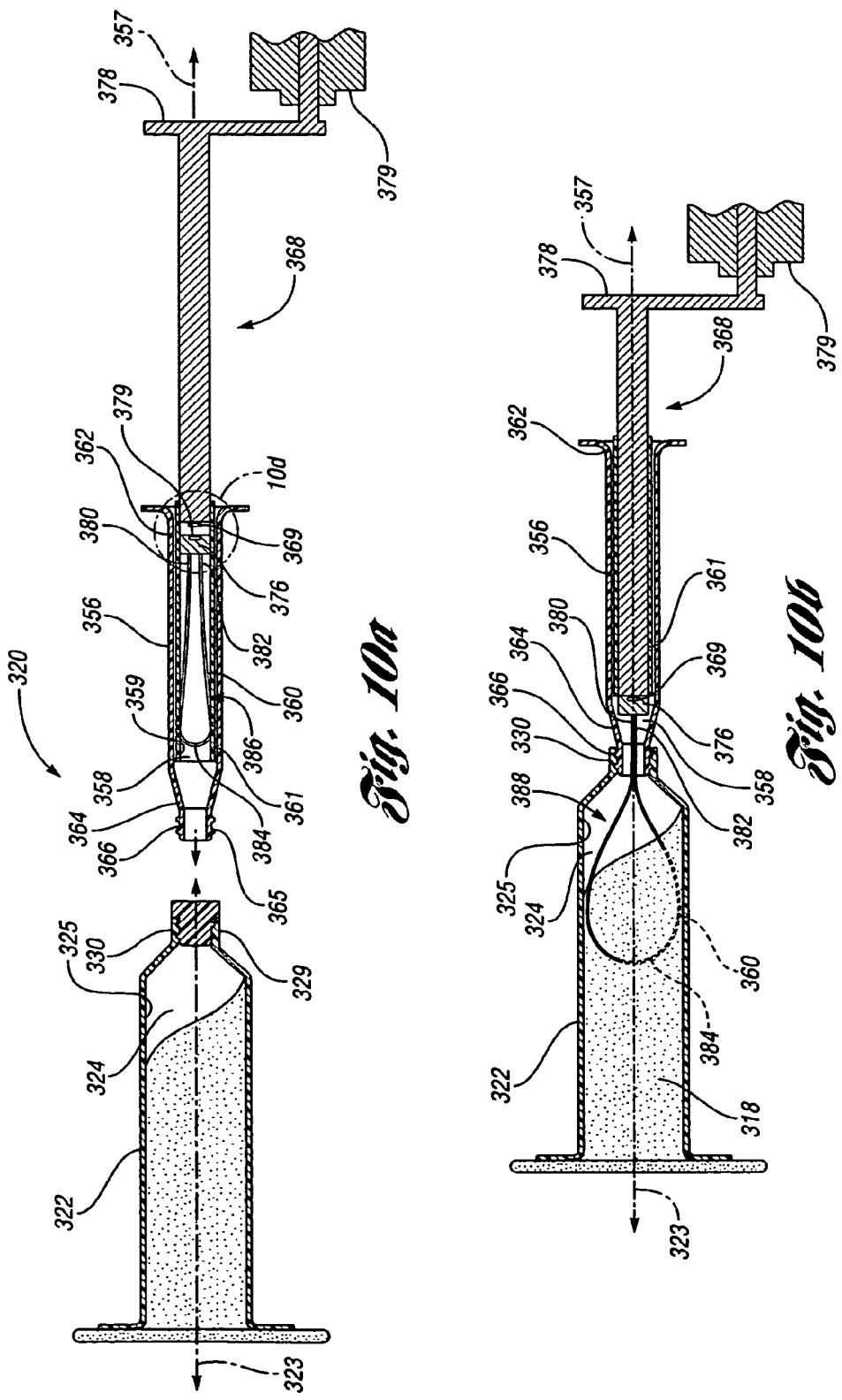

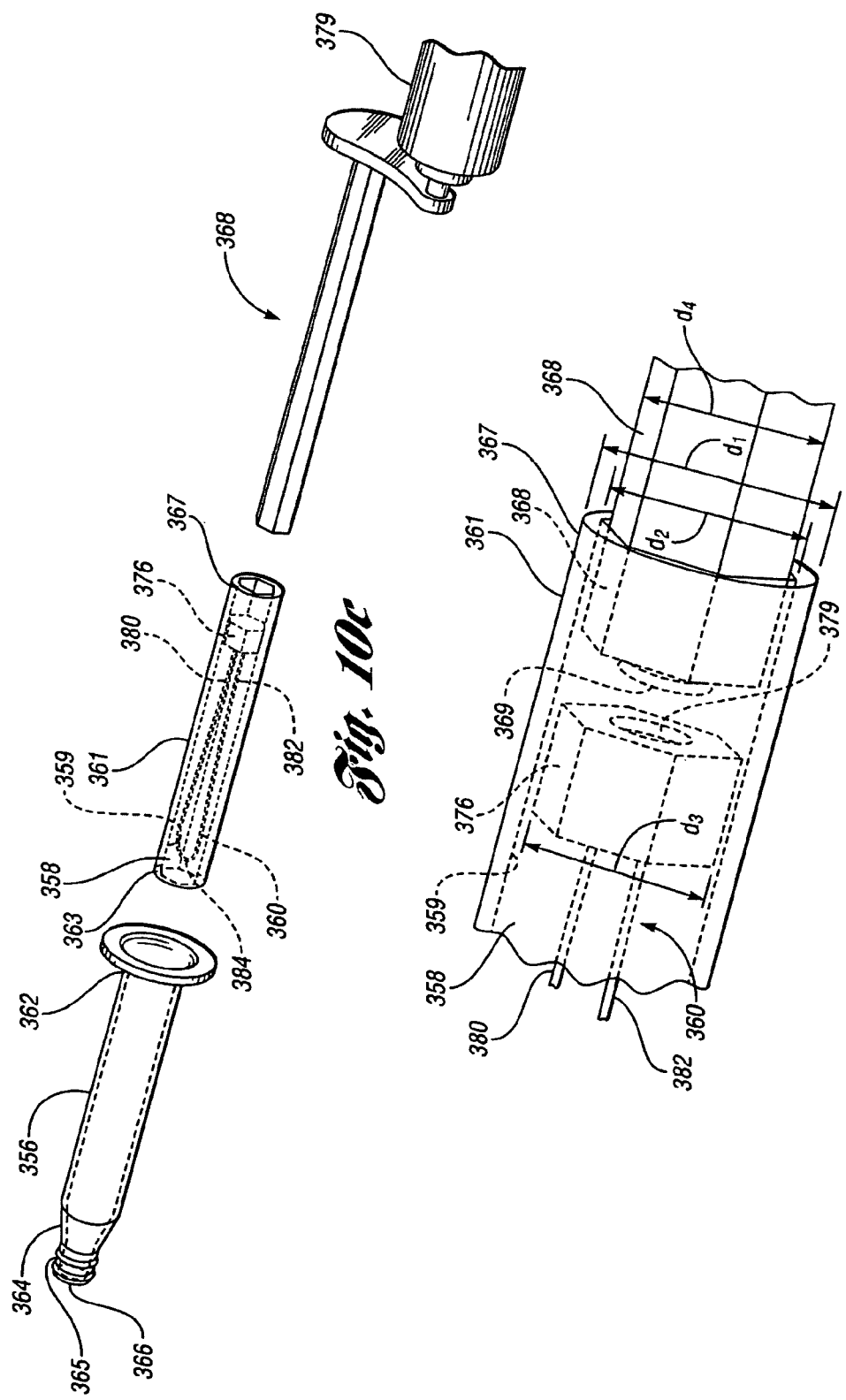

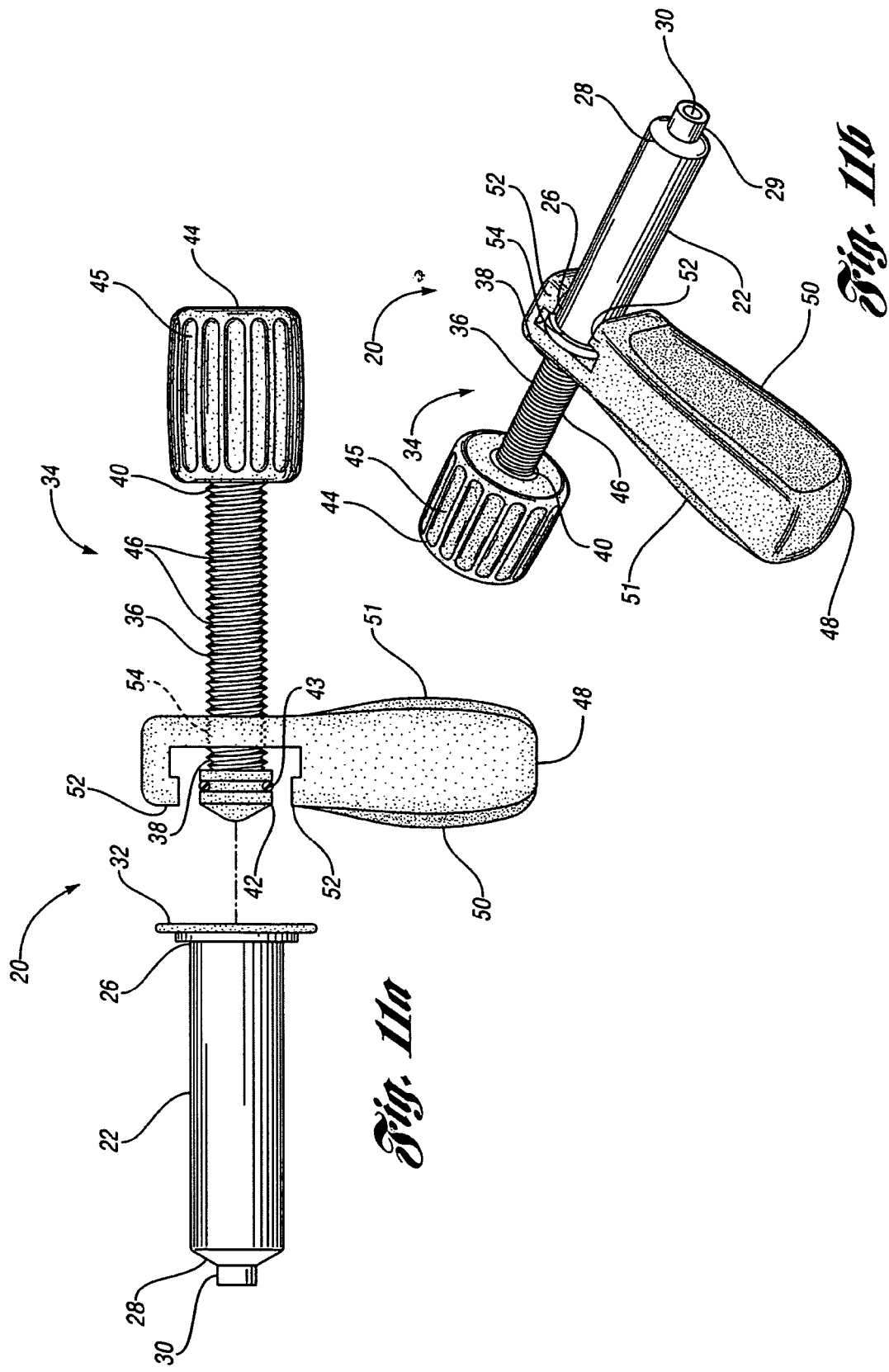

VERTEBROPLASTY ALL IN ONE MIXER

BACKGROUND OF THE INVENTION

1. Field of the Invention

The present invention relates to a device, a kit and a method for mixing and dispensing a bone cement mixture.

2. Description of Related Art

There is a clinical need to fill and stabilize damaged bones of patients, such as for example, filling defects in collapsed vertebra of patients suffering from severe back pain caused by osteoporosis, metastatic tumors or back injuries. Currently, these defects are repaired using multi-component bone cements that are mixed in open containers, transferred to a device and injected into the damaged bone where the mixture chemically reacts or cures to form a solid support structure.

The most widely used bone cements are based on polymethylmethacrylate (PMMA) and hydroxyapatite. These materials have relatively good strength characteristics, but have a number of drawbacks. These cements are a two-part chemically reactive system and have approximately five to ten minutes of working time once the components are mixed. As for example with the PMMA based system, one of the components is a liquid monomer methylmethacrylate (MMA), which is noxious and toxic to handle. The other component, the polymer component PMMA, is a powder that can be difficult to mix thoroughly. Moreover, current methods of mixing these two components together are typically done by hand in an open container or dish. This procedure permits significant vaporization of the noxious liquid monomer MMA. Also, the working time increases between mixing and dispensing because once the mixture is mixed it then needs to be transferred to a syringe for injection into the damaged bone. Moreover, the working time is limited because the viscosity of the cement constantly increases during mixing, thus making transferring of the mixture to the syringe and injection of the mixture into the damaged bone more difficult. Often, very high injection pressures and/or large bore needles may be necessary to inject the mixture, especially if it is near the end of the cements working time.

Thus, there is a need to provide a device for both mixing and dispensing a bone cement mixture.

BRIEF SUMMARY OF THE INVENTION

Embodiments of the present invention provide a device, a kit and a method that facilitates mixing and dispensing of the bone cement mixture such that the interventionalist and the patient have minimal exposure to the noxious vapors of the monomer as well as providing more flexible working times for suitable injection-ability of the mixture into the damaged bone.

In at least one embodiment of the present invention, a device for mixing and dispensing a bone cement mixture is provided. The device comprises an injector housing having a proximal end, a distal end, and an first chamber formed therein for containing a first and a second bone cement component. A first outlet at the distal end is in fluid communication with the first chamber. The proximal end is configured to receive a first plunger. The device further comprises a mixing element housing having a proximal end, a distal end, and a second chamber formed therein for containing a mixing element. A second outlet at the distal end is in fluid communication with the second chamber. The proximal end is configured to receive a second plunger to advance the mixing element from the second chamber into the first chamber and to rotate the mixing element to mix the bone cement components together to form a bone cement mixture. After withdrawal of the mixing element from the first chamber of the injector housing, the first plunger actuates within the first chamber to dispense the bone cement mixture from the device.

In one embodiment, the mixing element is coupled to a stop member at the distal end of the second plunger.

In another embodiment, the mixing element is coupled to a stop member freely disposed and slidable within the second chamber. In this embodiment, the second plunger forms a mating fit with the first stop member to advance and rotate the mixing element.

In another embodiment, the mixing element is coupled to a stop member, such as a ball bearing, adjacent the second outlet of the mixing element housing. In this embodiment, the second plunger actuates within the second chamber to advance the mixing element from the second chamber into the first chamber until the second plunger meets the stop member. In this embodiment, the second plunger forms a mating fit with the stop member to rotate the mixing element.

In at least another embodiment of the present invention, a bone cement substitute kit for mixing a bone cement mixture and dispensing the bone cement mixture into a damaged bone of a patient is provided. The kit comprises a first bone cement component and a second bone cement component. The kit further comprises a device in accordance with an embodiment described above further comprising a device handle for assembly with the injector housing. The device handle includes a first end, a second end, and an opening formed between the first and second ends. The device handle supports the injector housing adjacent the opening at the first end. The opening receives the first plunger at the second end of the device handle. After withdrawal of the mixing element from the injector housing and assembly of the injector housing with the device handle, the first plunger actuates within the injector housing to dispense the bone cement mixture. In this embodiment, the kit further comprises a needle configured to be fluidly coupled to the first outlet for receiving the bone cement mixture from the device and advancing the bone cement mixture into the damaged bone of the patient.

In at least another embodiment of the present invention, a method for mixing a bone cement mixture and for dispensing the bone cement mixture into a damaged bone of a patient is provided. The method comprises introducing a first and a second bone cement component into a first chamber within an injector housing of a device in accordance with an embodiment described above. The method further comprises advancing the mixing element from the second chamber into the first chamber and mixing the first bone cement component with the second bone cement component within the first chamber to form the bone cement mixture. The mixing element is withdrawn from within the first chamber and the first plunger actuates within the first chamber to dispense the bone cement mixture from the first chamber into the damaged bone of the patient via a needle fluidly coupled with the injector housing.

Further objects, features and advantages of the invention will become apparent from consideration of the following description and the appended claims when taken in connection with the accompanying drawings.

BRIEF DESCRIPTION OF THE DRAWINGS

FIG. 7a is a partial side cross-sectional view of a device for mixing bone cement and stabilizing a collapsed vertebra in accordance with one embodiment of the present invention, the device shown with a mixing element in a stored configuration;

FIG. 7b is a partial side cross-sectional view of the device in FIG. 7a, the device shown with the mixing element in a mixing configuration;

FIG. 7c is a partial side cross-sectional view of a device for mixing bone cement and stabilizing a collapsed vertebra in accordance with another embodiment of the present invention, the device shown with a mixing element in a mixing configuration;

FIG. 8a is a partial side cross-sectional view of a device for mixing bone cement and stabilizing a collapsed vertebra in accordance with yet another embodiment of the present invention, the device shown with a mixing element in a stored configuration;

FIG. 8b is a partial side cross-sectional view of the device in FIG. 8a, the device shown with the mixing element in a mixing configuration;

FIG. 10a is a partial side cross-sectional view of a device for mixing bone cement and stabilizing a collapsed vertebra in accordance with yet another embodiment of the present invention, the device shown with a mixing element in a stored configuration;

FIG. 10b is a partial side cross-sectional view of the device in FIG. 10a, the device shown with the mixing element in a mixing configuration;

FIG. 10c is an exploded view of the mixing element housing of the device in FIGS. 10a-b, the mixing element housing shown with the mixing element in the stored configuration;

FIG. 10d is an enlarged view of section 10d of FIG. 10a;

FIG. 11a is a partial side view of a device for stabilizing a collapsed vertebra in accordance with another embodiment of the present invention;

FIG. 11b is partial side perspective view of the device in FIG. 11a;

FIG. 12b is an exploded view of the bone cement substitute kit depicted in FIG. 12a.

DETAILED DESCRIPTION OF THE INVENTION

Detailed embodiments of the present invention are disclosed herein. It is understood however, that the disclosed embodiments are merely exemplary of the invention and may be embodied in various and alternative forms. The figures are not necessarily to scale; some figures may be configured to show the details of a particular component. Therefore, specific structural and functional details disclosed herein are not to be interpreted as limiting but merely as a representative basis with the claims and for teaching one skilled in the art to practice of the present invention.

Examples of the present invention seek to overcome some of the concerns associated with stabilizing and/or repairing the damaged bone of a patient with a bone cement while minimizing toxic effects to both the patient and the interventionalist, and enhancing the ease of handling of the bone cement for both mixing and dispensing into the damaged bone.

Employing the principles of the present invention is, for example, a device, a kit, and a method for stabilizing and/or repairing a damaged bone of a patient. The device, which is utilized in both the kit and the method, is a closed mixing and dispensing system having an injector housing surrounding a first chamber and a mixing element housing surrounding a second chamber. The first chamber is configured to contain a first and a second bone cement component and the second chamber is configured to contain a mixing element which moves from the second chamber into the first chamber to mix the first and second bone cement components together to form a bone cement mixture. After the bone cement mixture is formed within the first chamber, the mixing element is withdrawn from the first chamber. The device may also be in fluid communication with a needle inserted into the damaged bone of a patient. The device is configured such that the bone cement mixture may be advanced from the device into the damaged bone of a patient via the needle.

The device preferably mixes the bone cement components together without releasing noxious monomer fumes contained in one of the bone cement components. Moreover, since the device is configured to dispense the bone cement mixture there is no need for transferring the mixture from another source into the device. Accordingly, the device minimizes the mixing and dispensing time of the bone cement and thus, enhances the remaining working time for introducing the mixture into the damaged bone. Once the bone cement is introduced into the damaged bone of the patient it cures to form a solid structure which stabilizes the bone.

Figure 1:
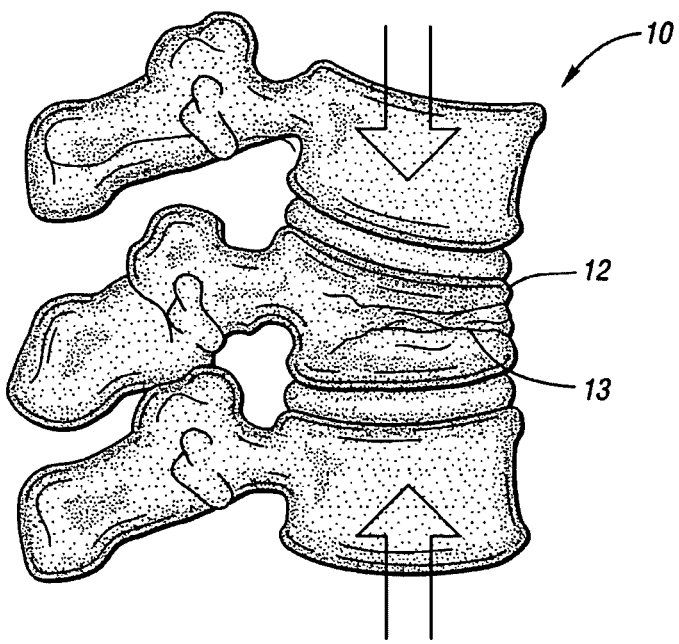
FIG. 1 is a partial side view of a collapsed vertebra.

Referring now to the drawings, FIG. 1 illustrates a vertebra 10 which includes a collapsed vertebra 12 with a compression facture 13. The vertebra 10 may be for example in the thoracic or lower spine of the patient. In the compression fracture 13 of the vertebra 12, the bone tissue of the vertebral body collapses. This condition is commonly caused by osteoporosis and less often by a tumor, or trauma to the back.

Figure 2:
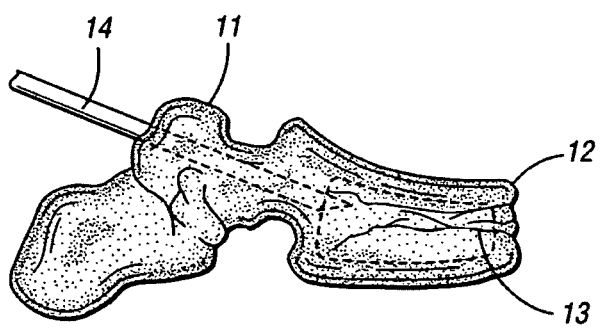
FIG. 2 is a partial side view of a device for stabilizing a collapsed vertebra in accordance with one embodiment of the present invention.
Figure 3:
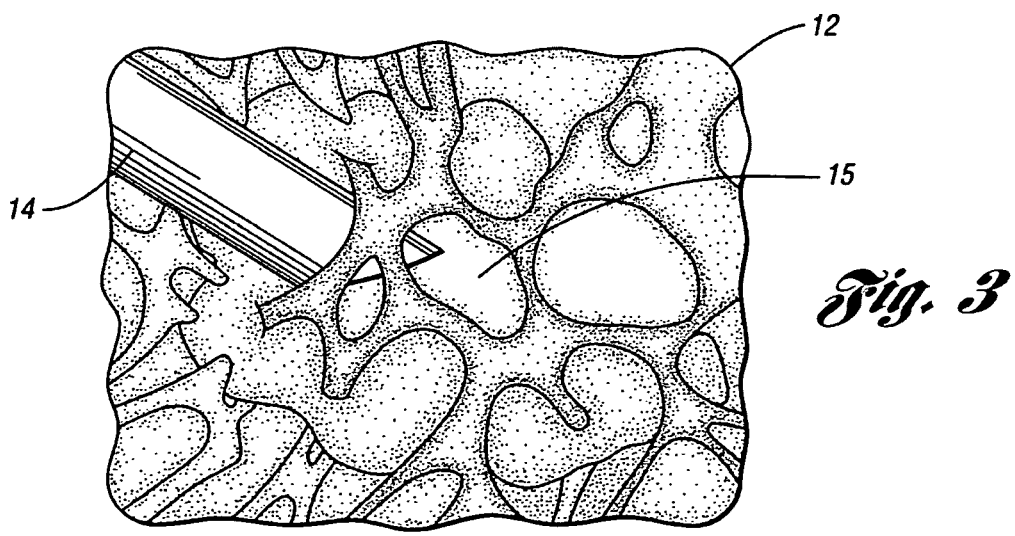
FIG. 3 is an enlarged view of FIG. 2.

Referring now to FIGS. 2 and 3, at least one embodiment of the present invention is provided. The collapsed vertebra 12 may be stabilized by either vertebroplasty or kyphoplasty, both of which are medical procedures for introducing bone cement into the collapsed vertebra. These procedures stabilize the collapsed vertebra by filling in open spaces within the vertebra 12 to provide a more continuous and solid form. Kyphoplasty may further stabilize the vertebra 12 by restoring vertebral spacing which alleviates nerve pinching from the vertebra 12. It should be noted that the present invention applies to both of these medical procedures and other procedures for stabilizing and/or repairing damaged bones of patients despite many of the various embodiments discussed herein are described using verteborplasty.

Vertebroplasty involves that a patient remain lying throughout the entire procedure. It is performed under a local anesthesia and/or a light sedative. A small nick is then made in the skin near the spine and a needle 14 is inserted percutaneously. As illustrated in FIG. 3, the needle 14 may be inserted into the interior open spaces 15 of the vertebra 12, for example through the left or right pedicle 11 of the vertebra 12.

Figure 4:
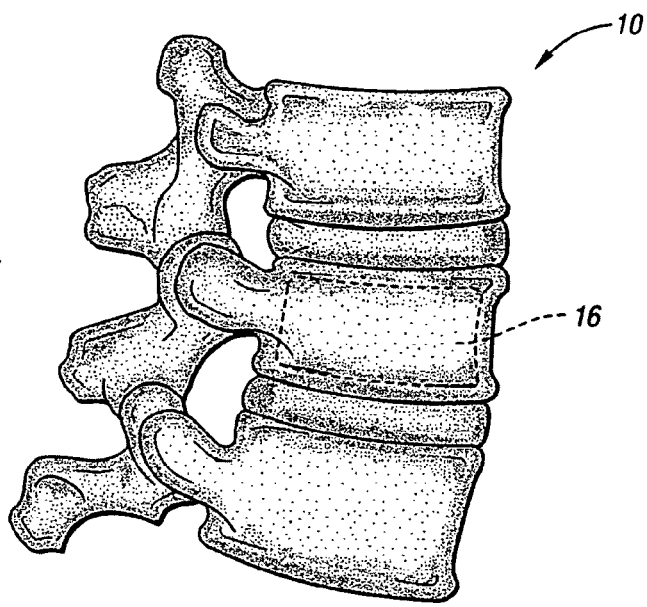
FIG. 4 is a partial side view of a stabilized collapsed vertebra in accordance with one example of the present invention.
Figure 5:
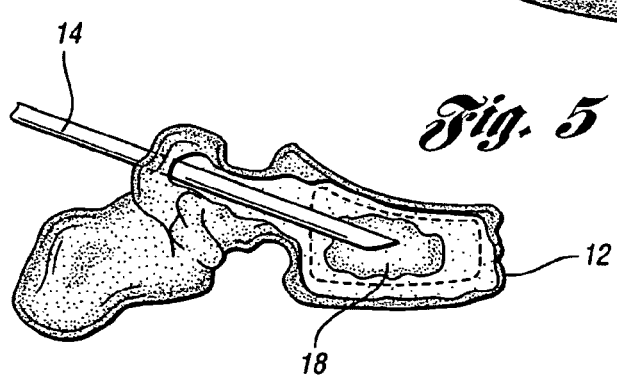
FIG. 5 is a partial side view of a device for stabilizing a collapsed vertebra in accordance with yet another embodiment of the present invention.

Referring to FIGS. 4 and 5, the bone cement mixture 18 may be dispensed from a device (not shown) through the needle 14 and into the vertebra 12 to form a solid structure 16 that supports the collapsed vertebra 12. The bone cement mixture 18 forms the solid structure 16 by chemically reacting or curing to become a solid. The stabilizing solid structure 16 may be formed within and/or about the collapsed vertebra 12 and may help restore vertebral spacing and alleviate nerve pinching by supporting the collapsed vertebra 12 generally in at least a compressive mode. Preferably, the structure substantially fills in the open spaces 15 of the collapsed vertebra 12 providing a more dense and continuous vertebra 12 which enhances mobility of the patient.

Referring to FIGS. 7-11, at least one embodiment of a device for mixing a bone cement mixture and for dispensing the mixture is provided. In all embodiments, the device 20, 120, 220, 320 or novel syringe comprises a respective injector housing 22, 122, 222, 322. The following description of the injector housing 20 also applies to the injector housing 120, 220, 320, wherein like numbers represent like elements.

As illustrated in FIGS. 7a-c, the injector housing 22 has a substantially cylindrical shape surrounding a chamber 24 disposed along a longitudinal axis 23. The injector housing 22 has a proximal end 26 and a distal end 28 and includes an outlet 30 at the distal end 28 in fluid communication with the chamber 24. A seal member, such as a cap 31, fits within the outlet 30 to seal the chamber 24 prior to mixing and dispensing the bone cement mixture 18. Another seal member, such as an adhesive peel-off tab 32, covers the opening at the proximal end 26. The chamber 24 is configured to contain a first bone cement component and a second bone cement component. For example, a bone cement system may be comprised of separate components A and B. These components may be a liquid and/or a solid, which when mixed together chemically react to form a solid structure. Component A may be initially contained in the chamber 24 and component B may be injected into the chamber 24 through the tab 32 at the proximal end 26 or through the outlet 30.

To further illustrate, component A, for example, may be a solid polymer powder of PMMA preloaded into the chamber 24 by the manufacturer of the device 20 and component B may be a liquid monomer MMA with a relatively low viscosity of about 0.6 centipoise at room temperature. The MMA could be poured from an external container into the chamber 24 or injected into the chamber 24, via a syringe, through the tab 32, prior to assembly of the injector housing 22 with an injector handle 48. Alternatively, the MMA could be injected into the outlet 30, via a syringe, through a luer fitting nozzle 29 at the distal end 28 of the chamber 24. When the MMA is mixed with the PMMA, a chemically reacting paste may be formed which continually increases in viscosity over a working time of about 5 to 10 minutes to form a solid structure. In another example, component A may be sodium phosphate and component B may be solid powder of monocalcium phosphate, tricalcium phosphate, calcium carbonate or mixtures thereof that form a chemically reacting solution when mixed with sodium phosphate, which also increases in viscosity over a working time of about 5 to 10 minutes to form a solid structure.

Providing an injector housing 22, in which the bone cement mixture 18 is mixed, and from which the bone cement mixture 18 is dispensed, substantially minimizes the fumes which result from vaporization of the noxious liquid monomer MMA. In addition, the sealed nature of the injector housing 22 helps minimize the noxious fumes. It is also possible to draw fumes into another syringe, through the tab 32 or the outlet 30, before removing the tab 32 and engaging the injector housing 22 with the injector handle 48.

In the embodiments illustrated in FIGS. 7a-c, the device 20 further comprises a mixing element housing 56 having a cylindrical shape surrounding a chamber 58 disposed along a longitudinal axis 57. The chamber 58 is configured to contain a mixing element 60. The housing 56 has a proximal end 62 and a distal end 64 and includes an outlet 66 at the distal end 64 in fluid communication with the chamber 58. In this embodiment, the mixing element 60 is coupled to a plunger 68, both of which are received by the proximal end 62 of the housing 56. The plunger 68 is configured to actuate within the chamber 58 to advance the mixing element 60 through the chamber 58 and into the chamber 24, and further to rotate the mixing element to mix the first and second bone cement components to form the bone cement mixture 18.

As shown in FIGS. 7a-c, the plunger 68 includes a plunger rod 70 having a distal end 72 and a proximal end 74. In this embodiment, a stop member 76 is disposed at the distal end 72 of the plunger rod 70 and a plunger handle 78 is disposed at the proximal end 74 of the plunger rod 70. The stop member 76 preferably includes a seal member, such as an o-ring 77, between the stop member 76 and the chamber wall 59 to facilitate movement of the stop member 76 within the chamber 58.

In this embodiment, the mixing element 60 is coupled to the stop member 76 such that the mixing element 60 moves with the stop member 76 as the plunger 68 actuates within the chamber 58. In this embodiment, the mixing element 60 is formed from a flexible elongate wire including first and second ends 80 and 82 both coupled to the stop member 76, forming a loop 84 between the first and second ends 80 and 82. As shown if FIGS. 7a-c, the first end 80 of the elongate wire 60 is connected to the stop member 76 and the second end 82 of the elongate wire 60 extends distally from the stop member 76, wherein the elongate wire 60 bends or curves such that the second end 82 extends proximally toward the stop member 76 and connects to the stop member 76, forming the loop 84 between the first and second ends 80 and 82, and distal the stop member 76.

In this embodiment, the chamber wall 59 of the mixing element housing 56 defines a smaller diameter than the diameter defined by the chamber wall 25 of the injector housing 22. Thus, the mixing element 60 is confined or compressed within the smaller diameter chamber 58, thereby defining a collapsed or stored configuration 86 of the mixing element 60.

In this embodiment, after the chamber 24 of the injector housing 22 has received the first and second bone cement components, the device 20 is positioned for mixing of the bone cement components. As illustrated in FIGS. 7b-c, the housings 22 and 56 are aligned such that the outlets 30 and 66 are adjacent and the axes 23 and 57 substantially coincide. Preferably, the outlet 30 of the injector housing 22 is sized to receive the outlet 66 of the mixing element housing 56 to allow for an easier introduction of the mixing element 60 into the chamber 24. For example, the luer fitting nozzle 29 may connect with a corresponding luer fitting nozzle 65 of the outlet 66 of the mixing element housing 56.

Once the housings 22 and 56 are positioned for mixing, the plunger handle 78 is manipulated to actuate the plunger 68 within the chamber 58 to advance the mixing element 60 in the stored configuration 86 from the chamber 58 to the chamber 24, wherein the mixing element 60 passes through respective outlets 66 and 30. For example, an interventionalist pushes the plunger handle 78 to the left in FIG. 7a, thus advancing the plunger 68 in a direction from the proximal end 62 toward the distal end 64 of the chamber 58. As the plunger 68 advances toward the distal end 64, the mixing element 60 moves with the stop member 76 and is advanced through the outlet 66 in its stored configuration 86, the outlet 66 compressing the mixing element 60 to allow the mixing element 60 to fit within the outlet 30 of the injector housing. As the mixing element 60 exits the outlet 66, it is received by the adjacent outlet 30 of the injector housing 22 and further advanced into the chamber 24. In this embodiment, the stop member 76 has a larger diameter than that of the outlet 66 and thus the stop member 76 stops proximal the outlet 66 when the mixing element 60 is fully deployed within the chamber 24.

As shown in FIGS. 7b-c, the mixing element 60 is advanced into the chamber 24 and expands to an expanded or mixing configuration 88 within the larger diameter chamber 24 of the injector housing 22. In the mixing configuration 88, the loop 84, formed between first and second ends 80, 82 of the mixing element 60, expands into an expanded balloon-like shape. In this embodiment, the plunger 68 rotates the mixing element 60 in the mixing configuration 88 about the longitudinal axes 23, 57 to mix the first and second bone cement components together within the chamber 24 to form the bone cement mixture 18. For example, an interventionalist turns the plunger handle 78 about the longitudinal axes 23, 57 to rotate the plunger 68 and thus the stop member 76 and the mixing element 60. As the mixing element 60 rotates within the chamber 24, the wire loop 84 cuts through the bone cement components and mixes the bone cement components into the bone cement mixture 18.

As illustrated in FIG. 7c, the mixing element 60 may include a wire loop 84 and an additional elongate wire having a first end 83 attached to the stop member 76 and extending to a second end 85 which forms a helically shaped blade when in the mixing configuration 88 to enhance the mixing ability of the mixing element 60.

After sufficient mixing of the bone cement mixture 18, the mixing element 60 is withdrawn from the chamber 24. For example, an interventionalist may pull the plunger 68 to the right in FIG. 7b, in a direction away from the housing 22, retracting the mixing element 60 back into the chamber 58, and thereafter pull the housing 56 away from the injector housing 22. Retracting the mixing element 60 back into the chamber 58, however, is not necessary. Rather, the interventionalist may simply pull the housing 56 away from the injector housing 22 to withdraw the mixing element 60 from the chamber 24 such that the outlet 30 compresses the loop 84 as the mixing element 60 is withdrawn from within the chamber 24 of the injector housing 22. Thereafter, the housing 56 and the mixing element 60 may be discarded.

Figure 8C:
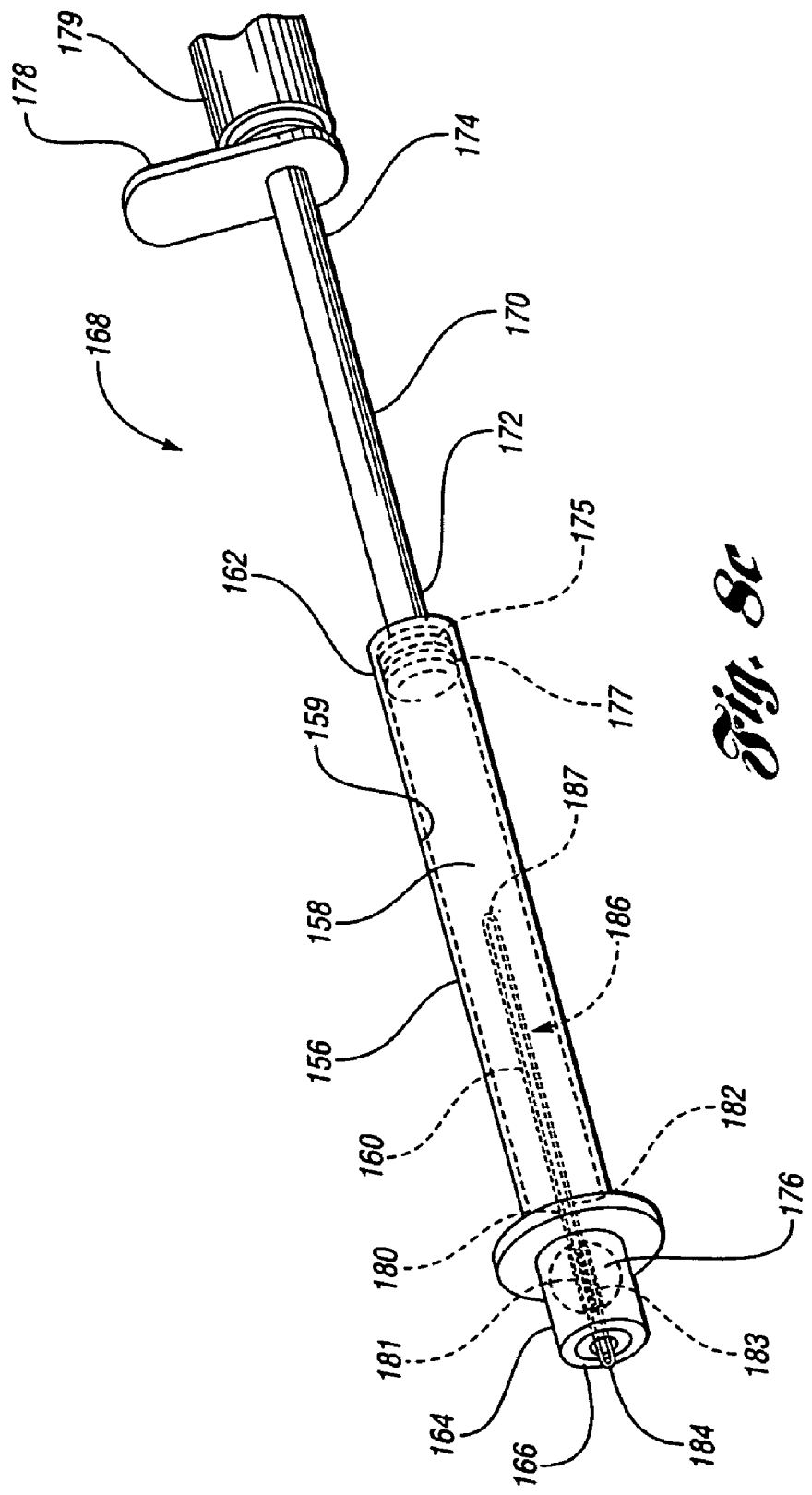
FIG. 8c is a side perspective view of the mixing element housing in FIG. 8a, shown with the mixing element in the stored configuration.

At least another embodiment of a device for mixing a bone cement mixture and for dispensing the mixture is provided in FIGS. 8a-c. As shown in FIGS. 8a-b, the device 120 or novel syringe comprises an injector housing 122 analogous to the injector housing 22 in FIGS. 7a-c, wherein like numbers refer to like elements throughout. As shown in FIGS. 8a-c, the device 120 further comprises a mixing element housing 156 having a substantially cylindrical shape surrounding a chamber 158 disposed along a longitudinal axis 157. The housing 156 has a proximal end 162 and a distal end 164 and includes an outlet 166 at the distal end 164 in fluid communication with the chamber 158. A stop member 176 is positioned within the chamber 158 adjacent the outlet 166 and a mixing element 160 is coupled to the stop member 176.

In this embodiment, the stop member 176 is, for example, a ball bearing having first and second channels 181 and 183 formed therethrough. In this embodiment, the mixing element 160 is formed from a flexible wire including first and second portions 180 and 182 which are received within the first and second channels 181 and 183 of the ball bearing 176, thus forming a distal wire loop 184 distal the ball bearing 176 and a proximal wire loop 187 extending proximal the ball bearing 176. In this embodiment, the mixing element housing 156 includes a chamber wall 159 defining a smaller diameter than the diameter defined by the chamber wall 125 of the injector housing 122. Thus, the mixing element 160 is confined or compressed within the smaller diameter chamber 158 when the mixing element 160 is housed within the chamber 158 of the mixing element housing 156, defining a collapsed or stored configuration 186.

As illustrated in FIGS. 8a-b, the proximal end 162 of the housing 156 receives a plunger 168 to advance the mixing element 160 from the chamber 158 to the chamber 124 of the injector housing 122 for mixing the bone cement components. In this embodiment, the plunger 168 includes a plunger rod 170 having a distal end 172 and a proximal end 174. The plunger 168 further includes a stop member 175 disposed at the distal end 172 of the plunger rod 170 and a plunger handle 178 at the proximal end 174 of the plunger rod 170. Preferably, the stop member 175 includes a seal member, such as an o-ring 177, between the stop member 175 and the chamber wall 159 to facilitate movement of the stop member 176 within the chamber 158.

In this embodiment, after the chamber 124 of the injector housing 122 has received the first and second bone cement components, the device 120 is positioned for mixing of the bone cement components. As illustrated in FIG. 8b, the housings 122 and 156 are aligned such that the outlets 130 and 166 are adjacent and the axes 123 and 157 substantially coincide. Preferably, the outlet 130 of the injector housing 122 is sized to receive the outlet 166 of the housing 156 to allow for an easier introduction of the mixing element 160 into the chamber 124. For example, the luer fitting nozzle 129 may connect with a corresponding luer fitting nozzle 165 of the outlet 166 of the mixing element housing 156.

Once the housings 122 and 156 are positioned for mixing, the plunger handle 178 is manipulated to actuate the plunger 168 within the chamber 158 to advance the mixing element 160 in the stored configuration 186 from the chamber 158 into the chamber 124, wherein the mixing element 160 passes through respective outlets 166 and 130. For example, an interventionalist may manually advance the plunger 168 toward the distal end 164 of the chamber 158. In another example, as shown in FIGS. 8a-c, the plunger 168 is coupled with an electric rotator 179 to electronically advance and rotate the plunger 168 and thereby relieve the interventionalist from having to manually manipulate the plunger 168. As the stop member 175 is advanced toward the distal end 164, the stop member 175 meets the proximal loop 187 of the mixing element 160 and advances the mixing element 160 toward the distal end 164 of the chamber 158.

In this embodiment, as the plunger 168 advances within the chamber 158, the stop member 175 pushes against the proximal loop 187 to advance the distal loop 184 into the chamber 124. Preferably, as the distal loop 184 is advanced within the chamber 158, the first and second portions 180 and 182 of the mixing element 160 move distally through the channels 181 and 183 formed within the ball bearing 176. The distal loop 184 is advanced through the outlet 166 in its stored configuration 186, the outlet 166 compressing the mixing element 160 to allow the mixing element 160 to fit within the outlet 130 of the injector housing 122, wherein the mixing element 160 is received within the adjacent outlet 130 of the injector housing 122. In this embodiment, the plunger 168 is advanced until the stop member 175 is adjacent the ball bearing 176 with only the proximal loop 187 in between the stop member 175 and the ball bearing 176, defining a fully deployed configuration of the mixing element 160.

As shown in FIG. 8b, the mixing element 160 is advanced into the chamber 124 and expands to an expanded or mixing configuration 188 within the larger diameter chamber 124 of the injector housing 122. In the mixing configuration 188, the distal loop 184 of the mixing element 160 expands into an expanded balloon-like shape. In this embodiment, the plunger 168 rotates the mixing element 160 in the mixing configuration 188 about the longitudinal axes 123, 157 to mix the first and second bone cement components together within the chamber 124 to form the bone cement mixture 118. Preferably, the stop member 175 is shaped to correspond with the shape of the ball bearing 176 such that the stop member 175 conformingly fits up against the ball bearing 176 when the mixing element 160 is fully deployed.

In this embodiment, the rotation of the plunger 168 and the stop member 175, via the electric rotator 179, rotates the ball bearing 176 due to the mating fit between the ball bearing 176 and the stop member 175. Preferably, the ball bearing 176 cooperates with the electric rotator 179 to provide the mixing element 160 with a faster rate of rotation, thereby enhancing the mixing of the bone cement components within the injector housing 122. As the mixing element 160 rotates within the chamber 124 of the injector housing 122, the distal loop 184 cuts through the bone cement components and mixes the bone cement components into the bone cement mixture 118.

After sufficient mixing of the bone cement mixture 118, the mixing element 160 is withdrawn from the chamber 124. In this embodiment, an interventionlist simply pulls the housing 156 away from the injector housing 122 to withdraw the mixing element 160 from the chamber 124 such that the outlet 130 compresses the wire loop 184 as the mixing element 160 is withdrawn from within the chamber 124 of the injector housing 122. Thereafter, the housing 156 and the mixing element 160 may be discarded.

Figure 9A:
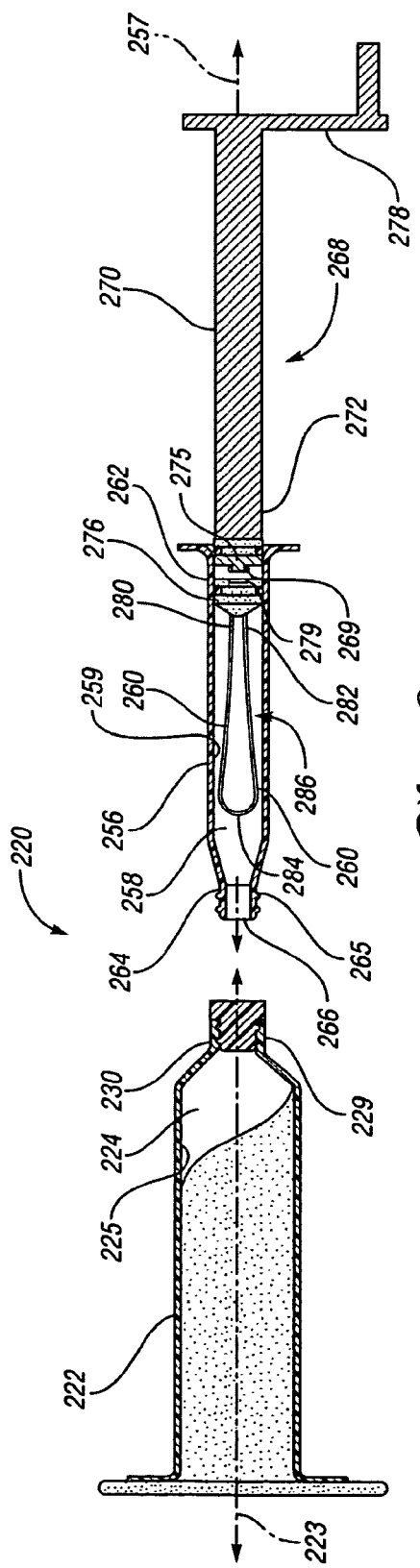
FIG. 9a is a partial side cross-sectional view of a device for mixing bone cement and stabilizing a collapsed vertebra in accordance with yet another embodiment of the present invention, the device shown with a mixing element in a stored configuration.
Figure 9B:
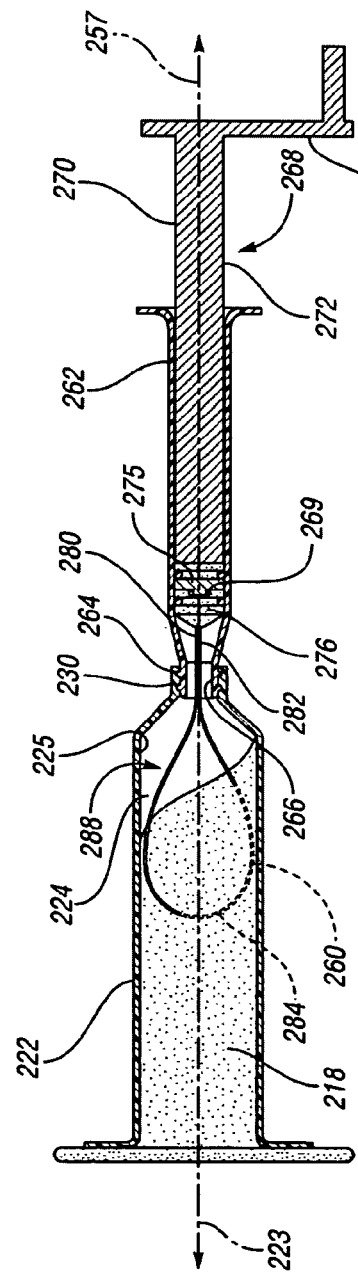
FIG. 9b is a partial side cross-sectional view of the device in FIG. 9a, the device shown with the mixing element in a mixing configuration.
Figure 9C:
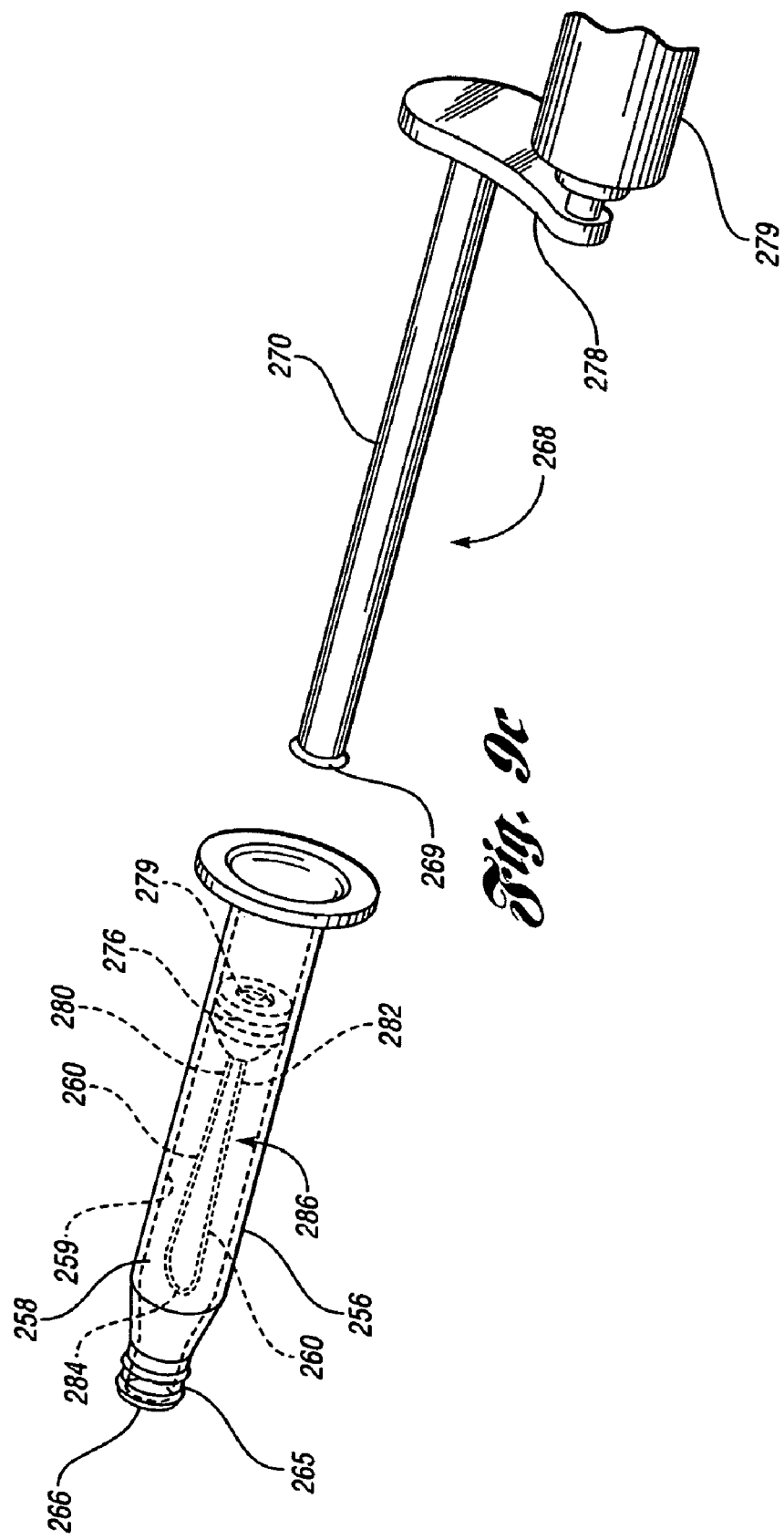
FIG. 9c is a side perspective view of a mixing element housing of a device in accordance with another embodiment of the present invention.

At least another embodiment of a device for mixing a bone cement mixture and for dispensing the mixture is provided in FIGS. 9a-c. As shown in FIGS. 9a-c, the device 220 or novel syringe comprises an injector housing 222 analogous to the injector housing 22 in FIGS. 7a-c, wherein like numbers refer to like elements throughout. As shown in FIGS. 9a-b, the device 220 further comprises a mixing element housing 256 having a substantially cylindrical shape surrounding a chamber 258 disposed along a longitudinal axis 257. The housing 256 has a proximal end 262 and a distal end 264 and includes an outlet 266 at the distal end 264 in fluid communication with the chamber 258. A stop member 276 is freely disposed within the chamber 258 and a mixing element 260 is coupled to the stop member 276.

In this embodiment, the proximal end 262 of the mixing element housing 256 receives a plunger 268 which engages the stop member 276 to advance the mixing element 260 from the chamber 258 into the chamber 224 of the injector housing 222, and further to rotate the mixing element 260 to mix the bone cement components together to form the bone cement mixture 218. In this embodiment, the plunger 268 forms a mating fit with the stop member 276 to advance and rotate the mixing element 260. As illustrated in FIGS. 9a-c, the plunger 268 includes a male mating member 269 which engages with a female mating member 279 formed in the stop member 276. For example, the female mating member 279 is a circular depression formed in the stop member 276 which receives and engages with a corresponding male mating member 269. The male mating member 269 may be a circular shaped projection formed on a stop member 275 connected to a distal end 272 of a plunger rod 270 of the plunger 268, as shown in FIGS. 9a-b.

In another example, shown in FIG. 9c, the male mating member 269 may be a cylindrical plunger rod 270 of the plunger 268 which engages with the female mating member 279. Preferably, the female mating member 279 includes an annular shoulder which engages a corresponding annular ring on the male mating member 269 as the male mating member 269 is inserted within the female mating member 279 to form a snap fit between the stop member 276 and the plunger 268.

As illustrated in FIGS. 9a-c, the mixing element 260 is coupled to the stop member 276 such that the mixing element 260 moves with the stop member 276 as the plunger 268 actuates within the chamber 258. In this embodiment, the mixing element 260 is formed from a flexible wire including first and second ends 280 and 282 both coupled to the stop member 276, forming a loop 284 in between the first and second ends 280 and 282. As shown in FIGS. 9a-c, the first end 280 of the elongate wire 260 is connected to the stop member 276 and the second end 282 of the elongate wire 260 extends distally from the stop member 276, wherein the elongate wire 260 bends or curves such that the second end 282 extends proximally toward the stop member 276 and connects to the stop member 276, forming the loop 284 between the first and second ends 280 and 282, and distal the stop member 276.

In this embodiment, the mixing element housing 256 includes a chamber wall 259 defining a smaller diameter than the diameter defined by the chamber wall 225 of the injector housing 222. Thus, the mixing element 260 is confined or compressed within the smaller diameter chamber 258 when the mixing element 260 is housed within the chamber 258 of the mixing element housing 256, defining a collapsed or stored configuration 286.

In this embodiment, after the chamber 224 of the injector housing has received the first and second bone cement components, the device 220 is positioned for mixing of the bone cement components. As illustrated in FIGS. 9a-b, the housings 222 and 256 are aligned such that the outlets 230 and 266 are adjacent and the axes 223 and 257 substantially coincide. Preferably, the outlet 230 of the injector housing 222 is sized to receive the outlet 266 of the mixing element housing 256 to allow for an easier introduction of the mixing element 260 into the chamber 224. For example, a luer fitting nozzle 229 of outlet 230 of the injector housing 222 may connect with a corresponding luer fitting nozzle 265 of outlet 266 of the mixing element housing 256.

Once the housings 222 and 256 are positioned for mixing, the plunger 268 is actuated within the chamber 258 to advance the mixing element 260 in the stored configuration 286 from the chamber 258 to the chamber 224, wherein the mixing element 260 passes through respective outlets 266 and 230. For example, an electric rotator 279 may be coupled with the plunger handle 278 to electronically advance and rotate the plunger 268. As the plunger 268 advances toward the distal end 264, the plunger 268 engages with the stop member 276 and advances the stop member 276. The mixing element 260 moves with the stop member 276 and is advanced through the outlet 266 in its stored configuration 286, the outlet 266 compressing the mixing element 260 to allow the mixing element 260 to fit within the outlet 230 of the injector housing 222. As the mixing element 260 exits the outlet 266, it is received by the adjacent outlet 230 of the injector housing 222 and further advanced into the chamber 224. In this embodiment, the stop member 276 has a larger diameter than that of the outlet 266 and thus the stop member 276 stops proximal the outlet 266 when the mixing element 260 is fully deployed within the chamber 224.

As shown in FIG. 9b, the mixing element 260 is advanced into the chamber 224 and expands to an expanded or mixing configuration 288 within the larger diameter chamber 224 of the injector housing 222. In the mixing configuration 288, the loop 284, formed between the first and second ends 280 and 282 of the mixing element 260, expands into an expanded balloon-like shape. In this embodiment, the plunger 268 cooperates with the stop member 276 to rotate the mixing element 260 in the mixing configuration 288 about the longitudinal axes 223, 257 to mix the first and second bone cement components together within the chamber 224 to form the bone cement mixture 218. As the mixing element 260 rotates within the chamber 224 of the injector housing 222, the wire loop 284 cuts through the bone cement components and mixes the bone cement components into the bone cement mixture 218.

After sufficient mixing of the bone cement mixture 218, the mixing element 260 is withdrawn from within the chamber 224. For example, the plunger 268 may be retracted in a direction away from the housing 222, retracting the mixing element 260 back into the chamber 258, and thereafter, the housing 256 may be pulled away from the injector housing 222. Retracting the mixing element 260 back into the chamber 258, however, is not necessary. Rather, the interventionalist may simply pull the mixing element housing 256 away from the injector housing 222 to withdraw the mixing element 260 from the chamber 224 such that the outlet 230 compresses the loop 284 as the mixing element 260 is withdrawn. Thereafter, the mixing element housing 256 and the mixing element 260 may be discarded.

At least another embodiment of a device for mixing a bone cement mixture and for dispensing the mixture is provided in FIGS. 10a-d. As shown in FIGS. 10a-b, the device 320 or novel syringe comprises an injector housing 322 analogous to the injector housing 22 in FIGS. 7a-c, wherein like numbers refer to like elements throughout. As shown in FIGS. 10a-d, the device 320 further comprises a mixing element housing 356 having a substantially cylindrical shape surrounding a chamber 358 disposed along a longitudinal axis 357. The housing 356 has a proximal end 362 and a distal end 364 and includes an outlet 366 at the distal end 364 in fluid communication with the chamber 358. A mixing element holder 361 containing a mixing element 360 is disposed within the mixing element housing 356 and surrounds the chamber 258. The holder 361 includes a cylindrical outer diameter $d_1$ such that the holder is received within the housing 356 and rotatable therein. The holder 361 includes a distal end 363 and a proximal end 367, which are aligned with respective distal and proximal ends 364, 362 of the housing 356 when the holder 361 is received within the mixing element housing 356.

In this embodiment, a stop member 376 is freely disposed within the chamber 358 surrounded by the mixing element holder 361. As shown in FIGS. 10a-d, the mixing element 360 is coupled to the stop member 376. In this embodiment, the proximal end 367 of the mixing element holder 361 receives a plunger 368 which engages the stop member 376 to advance the mixing element 360 from the chamber 358 into the chamber 324 of the injector housing 322, and further to rotate the mixing element 360 to mix the bone cement components together to form the bone cement mixture 318.

As illustrated in FIG. 10d, the holder 361 includes an inner diameter $d_2$ shaped and sized to correspond with an outer diameter $d_3$ of the stop member 376 such that the stop member 376 is slidable within the holder 361. In this embodiment, the plunger 368 includes an outer diameter $d_4$ shaped and sized to correspond with the inner diameter $d_2$ of the holder 361 such that the plunger 368 is slidably received within the holder 361 to advance the stop member 376 and the mixing element 360. Due to the mating fit between the outer diameters $d_3$ and $d_4$ of the stop member 376 and the plunger 368, respectively, with the inner diameter $d2$ of the holder 361, rotation of the plunger 368 rotates the holder 361 and the stop member 376, and thus the mixing element 360. As shown in FIG. 10d, the inner diameter $d_2$ of the holder 361, the outer diameter $d_3$ of the stop member 376, and the outer diameter $d_4$ of the plunger 368 have corresponding hexagonal shapes. It should be noted that the diameters $d_2$, $d_3$, and $d_4$ may have corresponding triangular, square, pentagonal, or any other shaped diameters such that the plunger 368 and the stop member 376 are slidable within the holder 361 and rotation of the plunger 368 rotates the holder 361 and the stop member 376.

Preferably, the plunger 368 forms a mating fit with the stop member 376 to aid in the advancement and rotation of the mixing element 360. As illustrated in FIGS. 10a-d, the plunger 368 includes a male mating member 369 which engages with a female mating member 379 formed in the stop member 376. For example, the female mating member 379 is a circular depression formed in the stop member 376 which receives and engages with a corresponding circular male mating member 369. In this embodiment, the female mating member 379 includes an annular shoulder which engages a corresponding annular ring on the male mating member 369 as the male mating member 369 is inserted within the female mating member 379 to forma a snap fit between the stop member 376 and the plunger 368.

As illustrated in FIGS. 10a-d, the mixing element 360 is coupled to the stop member 376 such that the mixing element 360 moves with the stop member 376 as the plunger 368 actuates within the chamber 358. In this embodiment, the mixing element 360 is formed from a flexible wire including first and second ends 380 and 382 both coupled to the stop member 376, forming a loop 384 in between the first and second ends 380 and 382. As shown in FIGS. 10a-c, the first end 380 of the elongate wire 360 is connected to the stop member 376 and the second end 382 of the elongate wire 360 extends distally from the stop member 376, wherein the elongate wire 360 bends or curves such that the second end 382 extends proximally toward the stop member 376 and connects to the stop member 376, forming the loop 384 between the first and second ends 380 and 382, and distal the stop member 376.

In this embodiment, the mixing element holder 361 includes a chamber wall 359 defining a smaller diameter than the diameter defined by the chamber wall 325 of the injector housing 322. Thus, the mixing element 360 is confined or compressed within the smaller diameter chamber 358 when the mixing element 360 is housed within the chamber 358 of the mixing element housing 356, defining a collapsed or stored configuration 386.

In this embodiment, after the chamber 324 of the injector housing has received the first and second bone cement components, the device 320 is positioned for mixing of the bone cement components. As illustrated in FIGS. 10a-b, the housings 322 and 356 are aligned such that the outlets 330 and 366 are adjacent and the axes 323 and 357 substantially coincide. Preferably, the outlet 330 of the injector housing 322 is sized to receive the outlet 366 of the mixing element housing 356 to allow for an easier introduction of the mixing element 360 into the chamber 324. For example, a luer fitting nozzle 329 of outlet 330 of the injector housing 322 may connect with a corresponding luer fitting nozzle 365 of outlet 366 of the mixing element housing 356.

Once the housings 322 and 356 are positioned for mixing, the plunger 368 is actuated within the chamber 358 to advance the mixing element 360 in the stored configuration 386 from the chamber 358 to the chamber 324, wherein the mixing element 360 passes through respective outlets 366 and 330. For example, an electric rotator 379 is coupled with the plunger 368 to electronically advance and rotate the plunger 368. As the plunger 368 advances toward the distal end 364, the plunger 368 engages with the stop member 376 and advances the stop member 376. The mixing element 360 moves with the stop member 376 and is advanced through the outlet 366 in its stored configuration 386, the outlet 366 compressing the mixing element 360 to allow the mixing element 360 to fit within the outlet 330 of the injector housing 322. As the mixing element 360 exits the outlet 366, it is received by the adjacent outlet 330 of the injector housing 322 and further advanced into the chamber 324. In this embodiment, the stop member 376 has a larger diameter than that of the outlet 366 and thus the stop member 376 stops proximal the outlet 366 when the mixing element 360 is fully deployed within the chamber 324.

In this embodiment, the mixing element 360 is advanced into the chamber 324 and expands to an expanded or mixing configuration 388 within the larger diameter chamber of the injector housing 322. In the mixing configuration 388, the loop 384, formed between the first and second ends 380 and 382 of the mixing element 360, expands into an expanded balloon-like shape. In this embodiment, the plunger 368 cooperates with the stop member 376 and the holder 361 to rotate the mixing element 360, via the electric rotator 379, in the mixing configuration 388 about the longitudinal axes 323, 357 to mix the first and second bone cement components together within the chamber 324 to form the bone cement mixture 318. As the mixing element 360 rotates within the chamber 324 of the injector housing 322, the wire loop 384 cuts through the bone cement components and mixes the bone cement components into the bone cement mixture 318.

After sufficient mixing of the bone cement mixture 318, the mixing element 360 is withdrawn from within the chamber 324. For example, the plunger 368 may be retracted in a direction away from the housing 322, retracting the mixing element 360 back into the mixing element housing 356, and thereafter, the housing 356 may be pulled away from the injector housing 322. Retracting the mixing element 360 back into the mixing element housing 356, however, is not necessary. Rather, the interventionalist may simply pull the mixing element housing 356 away from the injector housing 322 to withdraw the mixing element 360 from the chamber 324 such that the outlet 330 compresses the loop 384 as the mixing element 360 is withdrawn. Thereafter, the mixing element housing 356 and the mixing element 360 may be discarded.

The following description of the mixing element 60 with respect to the device 20 of FIGS. 7a-c applies to the mixing elements 160, 260, and 360 of the devices 120, 220, and 320 in FIGS. 8a-b, 9a-c, and 10a-d, respectively, wherein like numbers refer to like elements. In a preferred embodiment, the mixing element 60 is formed from shape memory materials or alloys, such as superelastic nickel-titanium alloys. An example of a suitable superelastic nickel-titanium alloy is Nitinol, which can "remember" and recover a previous shape. Nitinol undergoes a reversible phase transformation between a martensitic phase and an austenitic phase that allows it to "remember" and return to a previous shape or configuration. For example, compressive strain imparted to the mixing element 60 in the martensitic phase to achieve a low-profile delivery configuration (i.e., stored configuration 86), for transfer from the mixing element housing 56 to the injector housing 22 may be substantially recovered during a reverse phase transformation to austenite, such that the mixing element 60 expands to a "remembered" configuration (i.e., mixing configuration 88) for mixing the bone cement components within the chamber 24 of the injector housing 22. Typically, recoverable strains of about 8-10% may be obtained from superelastic nickel-titanium alloys. The forward and reverse phase transformations may be driven by a change in stress (superelastic effect) and/or temperature (shape memory effect).

The spring-like characteristic of the nitinol mixing element 60 allows the compressed wire loop 84 stored within the smaller diameter chamber 58 to expand within the larger diameter chamber 24 of the injector housing 22. In addition, the temperature induced shape memory property of the nitinol mixing element 60 allows for a variety of mixing elements having various shapes. For example, a nitinol wire mixing element may be formed with a helical blade at one end similar to that illustrated in FIG. 7c. In this configuration, the nitinol wire mixing element is straightened before being introduced into the chamber 58 of the mixing element housing 56. The nitinol wire mixing element in its straightened configuration is transferred from the chamber 58 to the chamber 24 of the injector housing 22 via the outlets 66 and 30. As the bone cement components A and B are mixed together, the chemical reaction produces a substantial amount of heat, causing the nitinol wire mixing element to return to its pre-formed helical shape.

As shown in FIG. 7c and described above, the mixing element 60 may include a wire loop 84 in addition to a wire formed with a helical blade to enhance the mixing ability of the mixing element 60. These shapes are merely examples of mixing elements 60 in accordance with the device 20 of the present invention. It should be understood that the heat produced from mixing the bone cement components may be used to form nitinol wire mixing elements 60 into a number of various preformed shapes beneficial for mixing the bone cement mixture 18. The mixing element 60 may be formed of any other suitable elastic or super-elastic material known in the art.

As illustrated in FIGS. 11a-b, the device 20, and similarly the devices 120, 220, and 320, wherein like numbers refer to like elements throughout, includes an injector handle 48 for gripping the device 20 by an interventionalist. After removal of the mixing element 60 from the chamber 24, and the peel-off tab 32 from the proximal end 26 of the injector housing 22, the injector housing 22 is assembled with the injector handle 48 for dispensing the bone cement mixture 18 from the injector housing 22. The cap 31 may be replaced to seal the outlet 30 during assembly of the injector housing 22 with the injector handle 48 and subsequently removed for dispensing the bone cement mixture 18. The injector handle 48 supports the injector housing 22, and thus the chamber 24, at its proximal end 26.

In this embodiment, the injector handle 48 includes a first end 50, an opposing second end 51, and a pair of flanges or tabs 52 at the first end 50 configured to receive and engage the proximal end 26 of the injector housing 22. The injector handle 48 further includes an opening 54 formed through the first and second ends 50, 51 configured to receive a plunger 34 at the second end 51. The proximal end 26 of the injector housing 22 is configured to receive the plunger 34 when the injector housing 22 is assembled with the injector handle 48. The plunger 34 actuates within the chamber 24 by moving within the chamber 24 toward the distal end 28 to dispense the bone cement mixture 18.

Preferably, the plunger 34 is a screw-gear plunger. The screw-gear plunger 34 includes a plunger rod 36 having a distal end 38 and a proximal end 40. In this embodiment, the screw-gear plunger 34 includes a stop member 42 disposed at the distal end 38 of the plunger rod 36 and a plunger handle 44 at the proximal end 40 of the plunger rod 36. The stop member 42 includes a seal member, such as an o-ring 43. When the injector housing 22 is engaged with the injector handle 48, the o-ring 43 is disposed between the stop member 42 and the chamber 24 for preventing bone cement from flowing therebetween and to facilitate movement of the stop member 42 within the chamber 24. The plunger rod 36 includes male threads 46 formed thereon.

In this embodiment, the screw-gear plunger 34 enters the opening 54 formed within the injector handle 48. The opening 54 is preferably threaded, including female threads configured to engage the threads 46 of the plunger rod 36. The stop member 42 may initially be detached from the plunger rod 36 before the plunger rod 36 enters the opening 54 at the second end 51. The stop member 42 may be reattached to the distal end 38 of the plunger rod 36 after the plunger rod 36 passes through the opening 54 of the injector handle 48.

In this embodiment, the injector housing 22 is received by the tabs 52 at the first end 50 of the injector handle 48 and the proximal end 26 receives the screw-gear plunger 34. Preferably, as the interventionalist turns the plunger handle 44, the threads 46 of the screw-gear plunger 34 and the mating threads of the opening 54 cooperate to advance the screw-gear plunger 34 into and through the chamber 24 from the proximal end 26 toward the distal end 28 to dispense the bone cement mixture 18 from the device 20 via the outlet 30.

In this embodiment, the chamber 24 is preferably a high pressure injection chamber adapted for withstanding positive displacement pressures associated with advancing "paste like" fluids through the outlet 30. In one example, the viscosity of the "paste like" fluid is greater than about 1,000 centipoise. The high pressure chamber 24 is preferably made of a plastic, such as polycarbonate, but may be made of glass or other suitable materials known in the art.

In at least one embodiment, the plunger handle 44 of the screw-gear plunger 34 is positioned at the proximal end 40 of the plunger rod 36 and disposed outside of the high pressure chamber 24 and has, for example, a cylindrical shape and a plurality of gripping indents 45 for facilitating gripping and turning of the screw-gear plunger 34 by the interventionalist.

Figure 6:
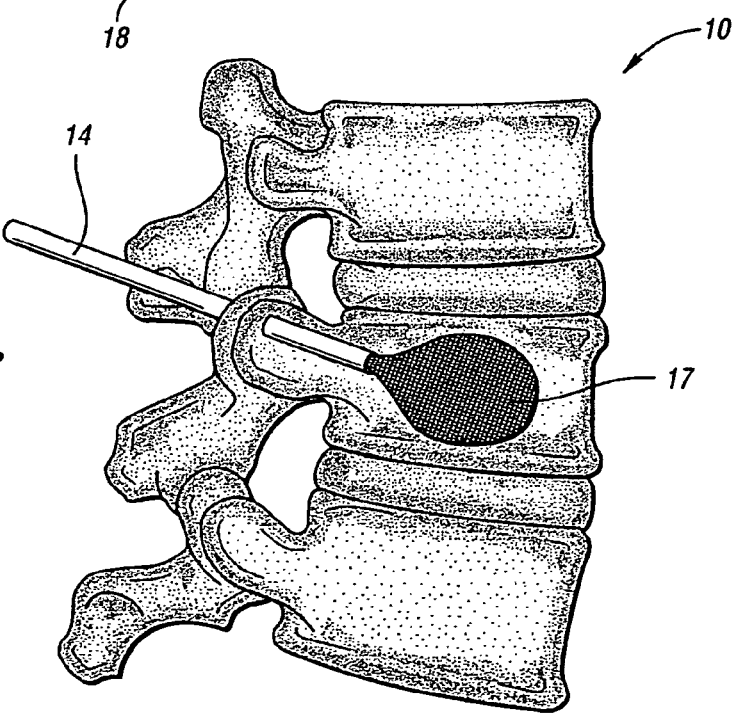
FIG. 6 is a partial side view of a device for stabilizing a collapsed vertebra in accordance with another embodiment of the present invention.

Referring to FIG. 6, at least one other embodiment for stabilizing a collapsed vertebra 12 of a patient is provided. A method for dispensing the bone cement mixture 18 into a damaged bone of a patient may include placing a balloon 17 into the collapsed vertebra 12. The balloon 17 may be positioned in the vertebra 12 for example via the needle 14, a catheter or mandrel. The balloon 17 is then filled with the bone cement mixture 18 and sealed. The balloon 17 may be sealed, for example, by twisting the needle 14 and shearing the corresponding end portion of the balloon 17 or, alternatively, by applying any suitable adhesive, such as a cyanoacrylate, to the end portion. The bone cement mixture within the sealed balloon 17 cures to form a solid support structure 16 within the collapsed vertebra 12.

In this embodiment, the balloon 17 may be made of any suitable material used for medical intracorporeal balloon devices. However, a polymer impermeable to body fluids and MMA may be preferred. An example of such material is polyethylene terephthalate (PET) or polybutylene terephthalate (PBT).

The interventionalist may also assess whether the collapsed vertebra 12 is sufficiently filled via fluoroscopy. If the collapsed vertebra 12 is not sufficiently filled, an additional balloon may be placed within the collapsed vertebra 12 and the filling, solidifying and/or curing and sealing steps may be repeated.

Figure 12A:
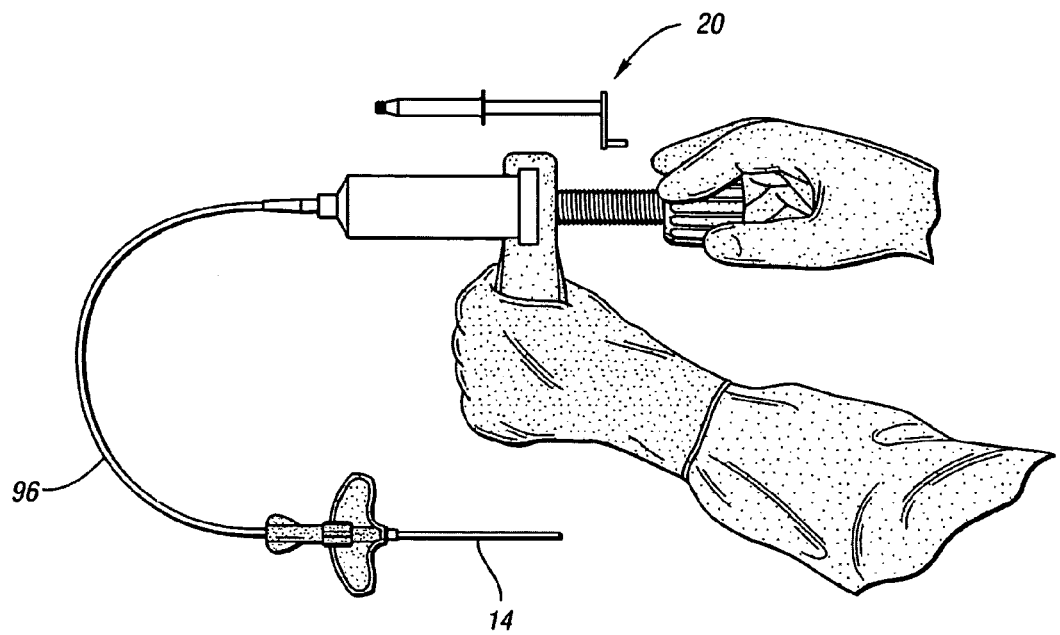
FIG. 12a is a side view of a bone cement substitute kit in accordance with one embodiment of the present invention.
Figure 12B:
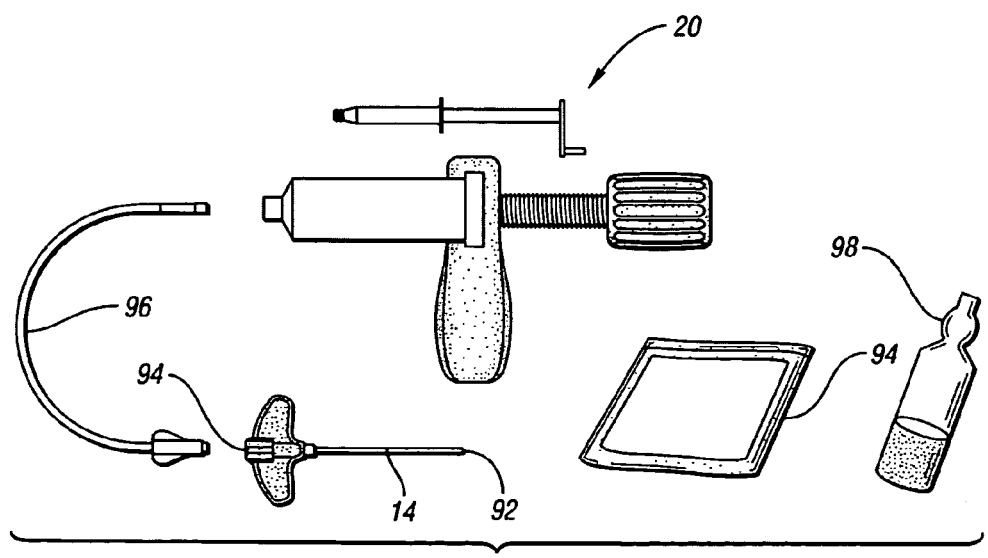

Referring also to FIGS. 12a-b, at least one embodiment of a bone cement substitute kit is provided. The kit includes a device 20 as discussed in the forgoing paragraphs (or similarly a device 120, 220, 320, wherein like numbers refer to like elements), as well as the needle 14 which is configured for fluid communication with the device 20 and for advancing the bone cement mixture 18 into the collapsed vertebra 12. The needle 14 may have a beveled edge end 92 for easy insertion and removal from the collapsed vertebra 12. The other end 94 of the needle 14 may be directly coupled to the device 20 or indirectly coupled via tubing 96. The tubing 96 provides fluid communication between the device 20 and the needle 14. Preferably, the tubing 96 may be flexible to facilitate maneuvering of the device 20 during injection of the bone cement into the damaged bone.

The kit may further comprise a sealed envelope 97 containing a component of the bone cement, such as PMMA, and sealed container 98 containing the other component of the bone cement, such as MMA. Alternatively, either of the first and second components of the bone cement may already be contained within the chamber 24 of the device 20 as packaged. The device 20 may include a valve which closes off fluid communication between the chamber 24 and the outlet 30 to facilitate packaging and handling of the kit when a bone cement component is pre-packaged within the chamber 24. Additionally, the kit may further include a balloon 17 (shown in FIG. 6) for receiving the bone cement mixture 18.

Figure 13:
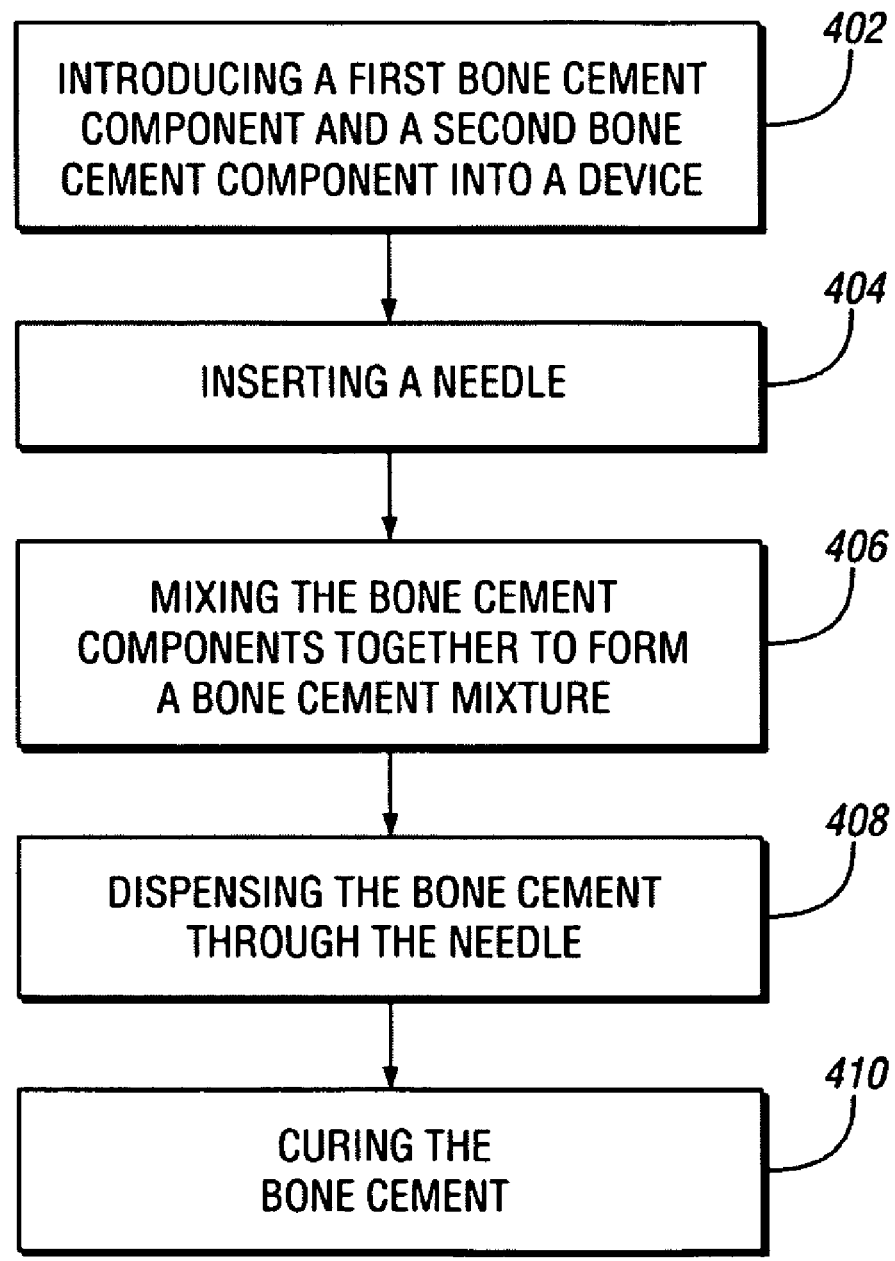
FIG. 13 is a flow chart for a method for stabilizing a damaged bone of a patient in accordance with an embodiment of the present invention.

Referring to FIG. 13, a method for mixing a bone cement mixture and dispensing the bone cement mixture into a damaged bone of a patient is provided. The method includes introducing a first bone cement component and a second bone cement component into a first chamber of a first housing of a device (402) as discussed in the forgoing paragraphs.

The first and second bone cement components are mixed together (404) to form a bone cement mixture. This includes aligning a second housing containing a mixing element with the first housing containing the bone cement components and actuating a plunger within the second chamber of the second housing to advance the mixing element into the first chamber and further actuating the plunger within the second chamber to rotate the mixing element within the first chamber about a longitudinal axis to mix the bone cement components. Actuating the plunger to advance the mixing element into the first chamber includes manipulating a plunger handle of the plunger to advance the plunger and thus the mixing element through the second chamber and into the first chamber via second and first outlets of the second and first housings. Actuating the plunger to rotate the mixing element includes turning the plunger handle.

A needle in fluid communication with the device is inserted (406) into the damaged bone of the patient.

The bone cement mixture is dispensed from the device into the damaged bone of the patient via the needle (408). This includes withdrawing the mixing element from the first chamber through the outlet of the first chamber. The plunger within the first chamber is then actuated to advance through the chamber to dispense the bone cement mixture from the chamber and through the needle. Actuating the plunger to advance through the chamber of the device includes manipulating a plunger handle of the plunger to advance the plunger through the first chamber to dispense the bone cement mixture out the outlet of the chamber. The bone cement mixture is then allowed to cure (410) to stabilize the damaged bone of a patient.

The method may further comprise positioning a balloon within the damaged bone of the patient, wherein dispensing the bone cement mixture includes receiving the bone cement mixture into the balloon via the needle.

As a person skilled in the art will readily appreciate, the above description is meant as an illustration of the implementation of the principles of this invention. This description is not intended to limit the scope or application of this invention in that the invention is susceptible to modification variation and change, without departing from the spirit of this invention, as defined in the following claims.

The invention claimed is:

1. A device for mixing and dispensing a bone cement mixture, the device comprising:
    a first cylindrical housing having a proximal end, a distal end, and a first chamber formed therein for containing a first and a second bone cement component, the distal end including a first outlet in fluid communication with the first chamber, the proximal end configured to receive a first plunger;
    a second cylindrical housing having a proximal end, a distal end, and a second chamber formed therein for containing a mixing element, the distal end including a second outlet in fluid communication with the second chamber, wherein the proximal end receives a second plunger to advance the mixing element from the second chamber through the second outlet and into the first chamber through the first outlet, wherein the second plunger rotates the mixing element to mix the first and second bone cement components together within the first chamber to form the bone cement mixture, and wherein the first plunger actuates within the first chamber to dispense the bone cement mixture from the first chamber through the first outlet after withdrawal of the mixing element therefrom, wherein the mixing element includes a first configuration and a second configuration, wherein the mixing element is in the first configuration when the mixing element is advanced from the second chamber into the first chamber, wherein the mixing element is in the second configuration when the mixing element mixes the bone cement mixture within the first chamber.

2. The device of claim 1, wherein each of the first and second housings includes a longitudinal axis, wherein the first and second housings are aligned such that the first and second outlets are adjacent and the longitudinal axes are coincident when the mixing element is advanced from the second chamber into the first chamber to mix the bone cement mixture.

3. The device of claim 1, wherein the first chamber includes a first chamber wall having a first diameter and the second chamber includes a second chamber wall having a second diameter smaller than the first diameter, wherein the mixing element is compressed to the first configuration within the second chamber, wherein the mixing element expands to the second configuration within the first chamber.

4. The device of claim 1, wherein the mixing element is coupled to a stop member.

5. The device of claim 4, wherein the stop member is part of the second plunger, the stop member disposed at a distal end of the second plunger, wherein the mixing element includes first and second ends coupled to the stop member forming a loop in between the first and second ends.

6. The device of claim 4, wherein the stop member is part of the second plunger, the stop member disposed at a distal end of the second plunger, wherein the mixing element includes a first end coupled to the stop member and a second end which forms a helical shape when the mixing element is in the second configuration.

7. The device of claim 4, wherein the stop member is freely disposed within the second chamber.

8. The device of claim 7, wherein the mixing element includes first and second ends coupled to the stop member forming a loop in between the first and second ends.

9. The device of claim 7, wherein the mixing element includes a first end coupled to the stop member and a second end which forms a helical shape when the mixing element is in the second configuration.

10. The device of claim 7, further comprising a mixing element holder disposed within the second cylindrical housing, the holder surrounding the second chamber and the mixing element coupled to the stop member, wherein the holder includes a cylindrical first outer diameter such that the holder is rotatable within the second cylindrical housing, wherein the holder includes an inner diameter shaped to correspond with a second outer diameter of the stop member such that the stop member is slidable within the holder, wherein the second plunger includes a third outer diameter shaped to correspond with the inner diameter of the holder such that the second plunger is slidable within the holder to advance the stop member and the mixing element, wherein the second outer diameter of the stop member and the third outer diameter of the second plunger form a mating fit with the inner diameter of the holder such that rotation of the second plunger rotates the holder, the stop member, and the mixing element.

11. The device of claim 10, wherein the inner diameter of the holder, the second outer diameter of the stop member, and the third outer diameter of the second plunger are shaped in the form of one of a triangle, a square, a pentagon, and a hexagon.

12. The device of claim 7, wherein the stop member is a ball bearing adjacent the second outlet, wherein the mixing element is an elongate wire, wherein the ball bearing includes first and second channels for receiving first and second portions of the elongate wire forming a first loop distal the stop member and adjacent the second outlet, the first and second portions extending proximally to form a second loop proximal the ball bearing, wherein the second plunger engages with the second loop to distally advance the mixing element through the second chamber, wherein the first and second portions of the elongate wire distally advance through the first and second channels within the ball bearing until the second plunger meets the ball bearing such that the second loop is disposed between the second plunger and the ball bearing and the first loop is disposed within the first chamber defining a fully deployed state of the mixing element, wherein the second plunger forms a mating fit with the ball bearing such that rotation of the second plunger rotates the ball bearing and the mixing element.

13. The device of claim 7, wherein the second plunger forms a mating fit with the stop member to at least one of advance the mixing element and rotate the mixing element.

14. The device of claim 8, wherein the second plunger includes a male mating member for engaging a female mating member formed within the stop member.

15. The device of claim 1 further comprising a device handle having a first end, a second end, and an opening formed therethrough, wherein the handle supports the first housing at the first end adjacent the opening, wherein the opening receives the first plunger at the second end of the handle and the first plunger passes through the opening into the first housing to dispense the bone cement mixture.

16. The device of claim 1 further comprising an electric rotator coupled to the second plunger, wherein the electric rotator cooperates with the second plunger to advance and rotate the mixing element.

17. The device of claim 1, wherein the second plunger includes a seal member that travels with the second plunger along the second housing.

18. A device for mixing and dispensing a bone cement mixture, the device comprising:
    a first cylindrical housing having a proximal end, a distal end, and a first chamber formed therein for containing a first and a second bone cement component, the distal end including a first outlet in fluid communication with the first chamber, the proximal end configured to receive a first plunger;
    a second cylindrical housing having a proximal end, a distal end, and a second chamber formed therein for containing a mixing element, the distal end including a second outlet in fluid communication with the second chamber, wherein the proximal end receives a second plunger to advance the mixing element from the second chamber through the second outlet and into the first chamber through the first outlet, wherein the second plunger rotates the mixing element to mix the first and second bone cement components together within the first chamber to form the bone cement mixture, and wherein the first plunger actuates within the first chamber to dispense the bone cement mixture from the first chamber through the first outlet after withdrawal of the mixing element therefrom, wherein the mixing element is an elongate wire.

19. The device of claim 18, wherein the elongate wire is formed from nitinol.

20. A bone cement substitute kit for mixing a bone cement mixture and dispensing the bone cement mixture into a damaged bone of a patient, the kit comprising:
    a first bone cement component and a second bone cement component;
    a device including:
        a first cylindrical housing having a proximal end, a distal end, and a first chamber formed therein for containing the first and second bone cement components, the distal end including a first outlet in fluid communication with the first chamber, the proximal end configured to receive a first plunger;
        a second cylindrical housing having a proximal end, a distal end, and a second chamber formed therein for containing a mixing element including an elongate wire, the distal end including a second outlet in fluid communication with the second chamber, wherein the proximal end receives a second plunger to advance the mixing element from the second chamber through the second outlet and into the first chamber through the first outlet, wherein the second plunger rotates the mixing element to mix the first and second bone cement components together within the first chamber to form the bone cement mixture, and wherein the first plunger actuates within the first chamber to dispense the bone cement mixture from the first chamber through the first outlet after withdrawal of the mixing element therefrom;
        a device handle having a first end, a second end, and an opening formed therethrough, wherein the handle supports the first housing at the first end adjacent the opening, wherein the opening receives the first plunger at the second end of the device handle and the first plunger passes through the opening into the first housing to dispense the bone cement mixture; and
        a needle configured to be fluidly coupled to the first outlet for receiving the bone cement mixture from the first chamber of the device and for advancing the bone cement mixture into the damaged bone of the patient.

21. The device of claim 20, wherein each of the first and second housings includes a longitudinal axis, wherein the first and second housings are aligned such that the first and second outlets are adjacent and the longitudinal axes are coincident when the mixing element is advanced from the second chamber into the first chamber to mix the bone cement mixture.

22. The device of claim 21, wherein the mixing element includes first and second ends forming a loop in between the first and second ends.

23. The device of claim 21, wherein the mixing element includes an end which forms a helical shape when the mixing element is in the second configuration.

24. A bone cement substitute kit for mixing a bone cement mixture and dispensing the bone cement mixture into a damaged bone of a patient, the kit comprising:
    a first bone cement component and a second bone cement component;
    a device including:
        a first cylindrical housing having a proximal end, a distal end, and a first chamber formed therein for containing the first and second bone cement components, the distal end including a first outlet in fluid communication with the first chamber, the proximal end configured to receive a first plunger;
        a second cylindrical housing having a proximal end, a distal end, and a second chamber formed therein for containing a mixing element, the distal end including a second outlet in fluid communication with the second chamber, wherein the proximal end receives a second plunger to advance the mixing element from the second chamber through the second outlet and into the first chamber through the first outlet, wherein the second plunger rotates the mixing element to mix the first and second bone cement components together within the first chamber to form the bone cement mixture, and wherein the first plunger actuates within the first chamber to dispense the bone cement mixture from the first chamber through the first outlet after withdrawal of the mixing element therefrom, wherein the mixing element includes a first configuration and a second configuration, wherein the mixing element is in the first configuration when the mixing element is advanced from the second chamber into the first chamber, wherein the mixing element is in the second configuration when the mixing element mixes the bone cement mixture within the first chamber;
        a device handle having a first end, a second end, and an opening formed therethrough, wherein the handle supports the first housing at the first end adjacent the opening, wherein the opening receives the first plunger at the second end of the device handle and the first plunger passes through the opening into the first housing to dispense the bone cement mixture; and a needle configured to be fluidly coupled to the first outlet for receiving the bone cement mixture from the first chamber of the device and for advancing the bone cement mixture into the damaged bone of the patient.

25. The device of claim 24, wherein each of the first and second housings includes a longitudinal axis, wherein the first and second housings are aligned such that the first and second outlets are adjacent and the longitudinal axes are coincident when the mixing element is advanced from the second chamber into the first chamber to mix the bone cement mixture.

26. The device of claim 24, wherein the mixing element includes first and second ends forming a loop in between the first and second ends.

27. The device of claim 24, wherein the mixing element includes an end which forms a helical shape when the mixing element is in the second configuration.

* * * * *